(12) United States Patent
Knipp et al.

(10) Patent No.: US 10,877,026 B2
(45) Date of Patent: Dec. 29, 2020

(54) BLOOD BRAIN BARRIER MODELS AND METHODS TO GENERATE AND USE THE SAME

(71) Applicant: Purdue Research Foundation, West Lafayette, IN (US)

(72) Inventors: Gregory T. Knipp, West Lafayette, IN (US); Aimable Ngendahimana, West Lafayette, IN (US); Christopher D. Kulczar, Bremen, IN (US); Kelsey E. Lubin, Lafayette, IN (US); Monika Lavan, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 387 days.

(21) Appl. No.: 15/697,699

(22) Filed: Sep. 7, 2017

(65) Prior Publication Data
US 2018/0067103 A1 Mar. 8, 2018

Related U.S. Application Data

(60) Provisional application No. 62/384,380, filed on Sep. 7, 2016.

(51) Int. Cl.
*G01N 33/50* (2006.01)
*C12N 5/079* (2010.01)
*C12N 5/071* (2010.01)

(52) U.S. Cl.
CPC ........ *G01N 33/5082* (2013.01); *C12N 5/0618* (2013.01); *C12N 5/0622* (2013.01); *C12N 5/0697* (2013.01); *G01N 33/5014* (2013.01); *G01N 33/5058* (2013.01); *C12N 2502/086* (2013.01); *C12N 2502/28* (2013.01); *C12N 2533/30* (2013.01)

(58) Field of Classification Search
CPC .......... G01N 33/5014; G01N 33/5058; G01N 33/5082; C12N 5/0618; C12N 5/0622; C12N 5/0697; C12N 2502/086; C12N 2502/28
See application file for complete search history.

(56) References Cited

U.S. PATENT DOCUMENTS

2017/0241988 A1* 8/2017 Prehaud ............... C12N 5/0622
2017/0283772 A1* 10/2017 Qian ..................... C12N 5/069

OTHER PUBLICATIONS

Nakagawa et al. "A new blood-brain barrier model using primary rat brain endothelial cells, pericytes and astrocytes" (2009), Neurochemistry International, vol. 54: 253-263. (Year: 2009).*

(Continued)

*Primary Examiner* — Teresa E Knight
(74) *Attorney, Agent, or Firm* — Purdue Research Foundation; Liang Zeng Yan

(57) ABSTRACT

The present disclosure generally relates to a process to prepare a cell culture system that mimics the structure of blood brain barrier (BBB) and are useful to study the functions thereof. In particular, the present invention relates to a direct-contact coculture and triculture systems prepared by plating BMECs on a pre-formed lawn of coculture of astrocytes and pericytes on the apical surface of a culture-chamber to achieve a truly direct contact triculture model for BBB. The cell culture systems disclosed herein are also useful for studying the functions of the blood brain barrier and predicting the efficacy and potential toxicity of a drug candidate.

21 Claims, 24 Drawing Sheets

(56) References Cited

OTHER PUBLICATIONS

A. Armulik, et al., "Pericytes regulate the blood-brain barrier." Nature, 2010, 468(7323): 557-561.
J. Banerjee, et al., "In vitro blood-brain barrier models for drug research" Drug Discovery Today 2016, 21(9): 1367-1386.
W.A. Banks, "From blood-brain barrier to blood-brain interface." Nat. Rev. Drug Discov. 2016, 15(4), 275-292.
S.M. Carl, et al., "ABC and SLC Transporter Expression and Pot Substrate Chracterization Across the Human CMEC/D3 Blood-Brain Barrier Cell Line" Mol Pharm. Aug. 2, 2010; 7(4): 1057-1068.
Eigenmann, et al., "Comparative study of four immortalized human brain capillary endothelial cell lines, hCMEC/D3, hBMEC, TY10, and BB19, and optimization of culture conditions, for an in vitro blood-brain barrier model for drug permeability studies" Fluids and Barriers of the CNS 2013, 10:33.
C.M. Garcia, et al., "Endothelial cell-astrocyte interactions and TGFh are required for induction of blood-neural barrier properties." Developmental Brain Research 152 (2004) 25-38.
K. Hatherell, et al., "Development of a three-dimensional, all-human in vitro model of the blood-brain barrier using mono-, co-, and tri-cultivation Transwell models." Journal of Neuroscience Methods 199 (2011) 223-229.
H.C. Helms, et al., "In vitro models of the blood-brain barrier: An overview of commonly used brain endothelial cell culture models and guidelines for their use." Journal of Cerebral Blood Flow & Metabolism 2016, vol. 36(5) 862-890.
G.T. Knipp, et al., "Paracellular Diffusion in Caco-2 Cell Monolayers: Effect of Perturbation on the Transport of Hydrophilic Compounds That Vary in Charge and Size." Journal of Pharmaceutical Sciences, 1997, 86(10), 1105.
N.J. Abbott, et al., "Structure and function of the blood-brain barrier." Neurobiology of Disease 37 (2010) 13-25.
D.J. Lindley, et al., "The Effects of Media on Pharmaceutically Relevant Transporters in the Human HT-29 Adenocarcinoma Cell Line" J Pharm Sci 101:1616-1630, 2012.
E.S. Lippmann, et al., "Derivation of blood-brain barrier endothelial cells from human pluripotent stem cells." Nature Biotechnology, 2012, 30(8), 783-793.

* cited by examiner

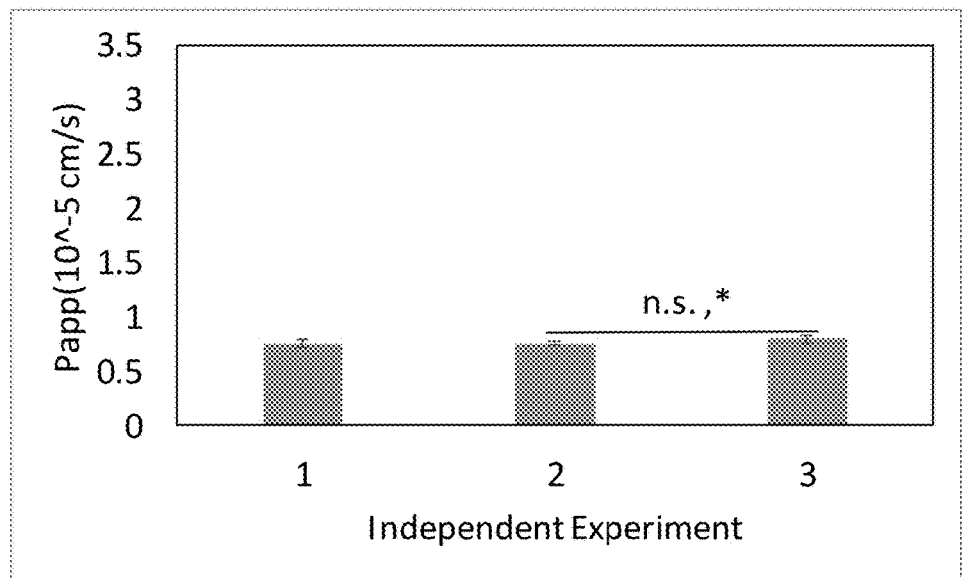
FIG. 25
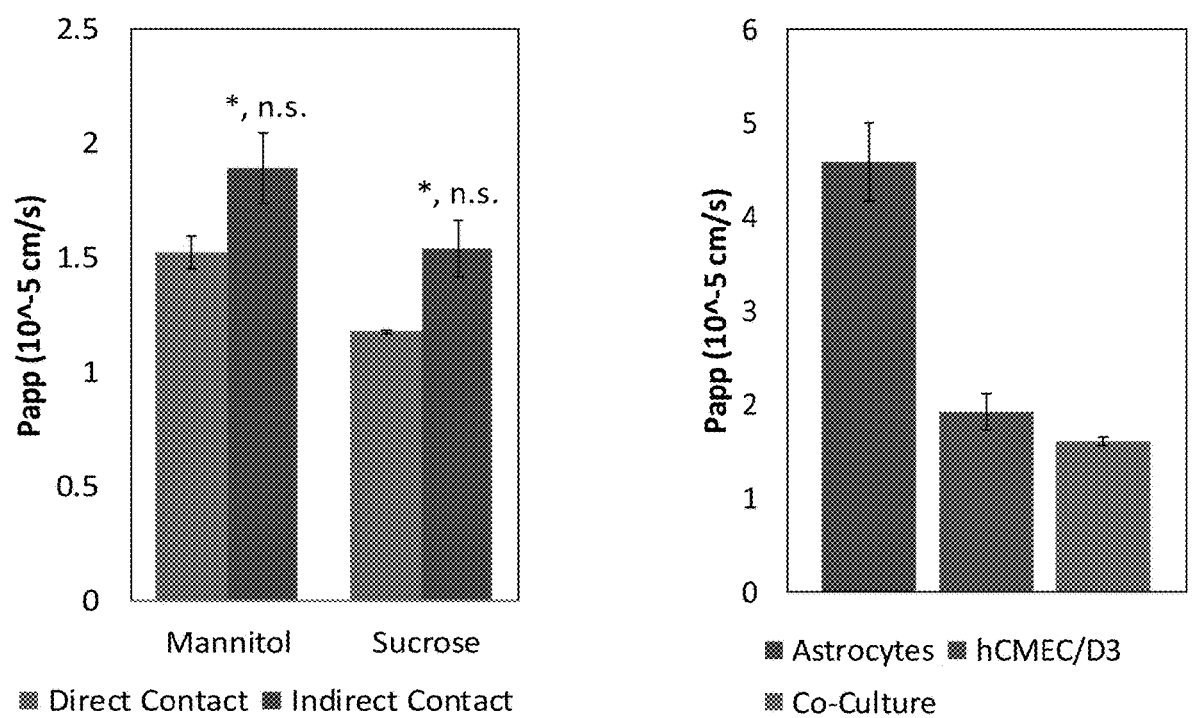
FIG. 26
FIG. 27

BLOOD BRAIN BARRIER MODELS AND METHODS TO GENERATE AND USE THE SAME

CROSS-REFERENCE TO RELATED APPLICATIONS

The present U.S. patent application is related to and claims the priority benefit of U.S. Provisional Patent Application Ser. No. 62/384,380, filed Sep. 7, 2016, the contents of which are hereby incorporated by reference in their entirety into this disclosure.

STATEMENT OF GOVERNMENT INTEREST

This invention was made with government support under GM065448 awarded by the National Institute of Health. The government has certain rights in the invention.

TECHNICAL FIELD

The present disclosure generally relates to a process to prepare a cell culture system that mimics the structure of blood brain barrier (BBB) and are useful to study the functions thereof. In particular, the present invention relates to direct-contact coculture and triculture systems prepared by plating brain microvessel endothelial cells (BMECs) of human or animal origin, primary, immortalized, normal or in a diseased state, or Human Brain Endothelial Cells (HBECs), on a pre-formed lawn of astrocytes and pericytes on the apical surface of a culture-chamber to achieve a truly direct contact triculture model for BBB. The coculture and triculture systems are useful for drug discovery and drug delivery screening efforts.

BACKGROUND

This section introduces aspects that may help facilitate a better understanding of the disclosure. Accordingly, these statements are to be read in this light and are not to be understood as admissions about what is or is not prior art.

The Blood Brain Barrier (BBB) was first reported in the late 1800s by Paul Erhlich, when he first noticed that certain staining dyes (hydrophilic dyes) could stain most body organs except the brain. Further studies by his student Edwin Goldmann proved that there was a barrier between the blood and the brain, which could not allow the passage of hydrophilic dyes (Ribatti, D., *J. Anat* 2006, 208(2): 139-152). After many years of research, it has been now established that brain capillaries are functionally and physiologically different from capillaries found in other parts of the central nervous system (CNS) and the body. (Banks 2016) A particularly important attribute of the BBB is that junctional complexes lining the paracellular space between the brain microvessel endothelial cells (BMECs) that form the capillary are comprised of distinct protein complexes that form a highly restrictive sieving barrier to the movement of most small and large hydrophilic molecules (Myers, M. G. *Ann Neurol.* 2013, 1(5), 409-417).

In addition, brain capillaries have little or no pinocytosis, possess a higher number of mitochondria (indicating higher metabolic requirements) and have a unique environment in which BMECs are almost completely surrounded by astrocytic end feet and pericytes (Turowski and Kenny, *Front Neurosci.* 2015, 9,156). Therefore, the uniqueness of the BMECs and their environment result in the formation of a physiologically dynamic barrier that restricts the transport of most therapeutic drugs designed to treat neurological disorders (Pardridge, W. *Expert Opin Drug Deliv,* 2016, 13(7): 963-975). A major challenge exists in modeling BBB permeation using simple and robust in vitro techniques.

Current in vitro techniques to model the BBB involve seeding BMECs on membranous filter support in as either a monolayer or in configuration with astrocytes and/or pericytes in the bottom chamber of Transwell® system (Banerjee, J. et al., *Drug Discov Today,* 2016, 21(9), 1367-1386). It is important to note that the BMECs can be derived from several different species including rats, bovine, and porcine sources (Helms, H. et al., *J. Cerebral Blood Flow Metabolism,* 2016, 36(5): 862-890). They can also be primary or transformed cells, which may further confound extrapolation to human BBB penetration (Syvanen, Lindhe et al. *Drug Metab Dispos,* 2009, 37(3): 635-643). In a monoculture configuration, the BMECs lack a physiologically relevant environment without biochemical signaling or physical interaction with supporting BBB cells such as astrocytes and pericytes. In many cases, an effort to introduce the BBB relevant environment in the in vitro models has been conducted by seeding either astrocytes or pericytes directly under the membranous filter support. However, this approach does not allow optimal (and physiologically representative) direct interactions between astrocytes, pericytes and endothelial cells as observed at the in vivo-BBB. The Transwell® filter support provides a significant limitation to the achievement of physical coverage and cell-cell connections formed, especially, between astrocytes and/or pericytes with the BMECs at the BBB in vivo when cultured in an indirect configuration. Furthermore, conventional indirect triculture, and even coculture, systems have been developed where either the astrocytes or pericytes are cultured on the bottom of the filter or alternatively pericytes or astrocytes, respectively, are cultured on the bottom of the basal chamber (Hatherell, Couraud et al. *J. Neurosci Methods,* 2011, 199 (2):223-229). While these models have provided significant reduction in permeability of paracellular markers, they still lack the extent of restriction and a physiologically representative BBB-configuration as found in vivo.

BRIEF SUMMARY OF THE INVENTION

This present disclosure relates to a direct-contact coculture and a triculture systems that are useful for studying the blood brain barrier (BBB). This direct-contact coculture and triculture systems exhibits a more physiologically representative configuration of the BBB-system in vivo. We have developed a triculture model of the BBB on the apical surface of a transwell chamber in a way that allows all the principal cellular components of the BBB-system to interact as they would do in their native in vivo environment, where brain microvessel endothelial capillaries are completely enwrapped by the astrocytes and partly by pericytes. The apical triculture system can be used to study the functions of BBB, and to predict the effectiveness of a novel drug candidate on its entry into the brain parenchyma.

In a parallel manner, a coculture model for the BBB on the apical surface of a Transwell system using BMECs and astrocytes is disclosed. The coculture system better mimics the BBB in neurological conditions in which pericytes may be lost from the BBB-system as it is the case of neurodegenerative disorders. In addition, pericytes tend to be lost with aging. Thus a coculture system may be more physiologically relevant for predicting drug transport across the BBB or neurotoxicity related to BBB-dysfunctions.

In some aspects, the present invention relates to a process of plating multiple cell types of the neurovascular unit in direct contact with one another, useful to study various aspects of the BBB as it pertains to drug screening, drug delivery, drug efficacy and toxicity, etc.

In some other aspects, the present invention relates to a process of plating multiple cell types in direct contact of coculture and triculture model systems with some representative cell type variations, including:
 a. The use of cells derived from different species (e.g. human, porcine, bovine, etc.);
 b. The use of cells types that are immortalized, primary, stem cell derived, or otherwise modified; and
 c. The use of cells from normal or diseased origin or otherwise modified to reflect a diseased state.

In some aspect, the present invention relates to a process of plating multiple cell types on a cell culture surface or support that those cells are in direct contact on the apical or basolateral surface of a permeable filter support, cell culture well plate, glass slide, or any other surface commonly used for cell culturing purposes.

The present disclosure also includes a novel method of use for an in vitro triculture BBB model that can be utilized for drug discovery and drug delivery screening efforts. The compositional properties of the model allow for either primary or proliferative astrocytes, pericytes, and BMECs to be cultured on the apical surface of a Transwell® chamber to form direct-contact interactions, which in some embodiments may be referred to as layers. The cell types may be collected from different species or origin in order to provide optimized conditions specific to the outcomes desired. In addition, the potential to perform assays where the triculture permeability can be linked to neuronal or other brain cell response can be monitored.

The innovation in the model disclosed herein lies in the unique configuration that the cells are cultured comparative to traditional triculture blood brain barrier in vitro methods. Briefly, approach disclosed herein enables a direct interaction of principal cellular components of the BBB system, namely supporting cells of the BBB, such as the astrocytes and pericytes, and BMECs cultured in optimized extracellular matrices (ECM) directly applied as a reagent and/or produced by the three cell types during the course of triculture growth. After the desired astrocyte and pericyte layer growth is reached, a source of BMECs at pre-optimized densities can be added and cultured to the desired level of confluency required to reach experimental goals. Here again, the layer of BMECs can be seeded on top of the supporting cells in the absence or presence of ECM substrates in order to reach the desired experimental properties and to form an optimized, physiologically relevant triculture BBB model.

Moreover, since pericytes and astrocytes may be found in capillaries perfusing other tissues within the body, the use of peripheral endothelial cells could be cultured in an analogous manner to study tissue specific outcomes. Another key feature is that primary cells may be collected and cultured from patients or animals of differing ages to assess the effects of ontogeny on permeation or neuronal cells.

The present disclosure therefore includes disclosure of at least the following:
 1) Apical and "direct-contact" triculture methodology
 2) Utility of the methods in drug discovery (small molecule, large molecule and biotechnology derived compounds), either in high through put or high content screening studies
 3) Utility of the methods in studying the transport properties of small and macromolecule (substrate) permeation across the BBB system
 4) Utility of the methods in the role of BBB system substrate permeation on resultant neurotoxicity
 5) Utility of the methods in modeling the role of BBB system substrate permeation in the mitigation of neurological diseases, e.g. Alzheimer primary BMECs, derived neurons or cancer cell lines derived from the brain.
 6) Utility of the methods in studying ontogeny of the BBB system utilizing primary or transformed cells derived from different age populations.
 7) Utility of the methods in evaluating drug delivery strategies to the brain
 8) Utility of the methods of inducing stem cell populations to reflect the BBB upon triculture.
 9) Utility of a similar approach to mimic perfusion across systemic endothelial cell populations with astrocytes and/or peripheral pericytes.
 10) Developing high throughput screening approaches for rapid screening of BBB penetration, efficacy, and/or neurotoxicity
 11) Modifying cell densities, media additives, and culture conditions to tailor the BBB triculture function to observe desired effects, e.g. increased transporter expression, increased tightness, etc.
 12) Utilizing primary or proliferative cell lines derived from different species to either mimic human BBB penetration or to identify factors that may be critical for extrapolation of in vitro and in vivo species specific results to humans.
 13) The utility of the co-culture model as a surrogate to delineate differences that may occur in aging or in diseases where either the pericyte or astrocyte densities may change. This may be applied as an alternative model to study all of the properties mentioned in the other claims.

A person of ordinary skill in the art may carry out plating the cells in direct contact at any reasonable cell density or with any variation of extra cellular matrix conditioning. For example, the cell seeding densities may be optimized differently for individual type and origin of a cell line according to the method disclosed herein. The amount of extracellular matrix that is used may be varied and optimized for the particular cell types being used. Additionally, variation of the overall density or confluency of each cell line may be manipulated to mimic a specific disease state.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 2A shows the configuration involves seeding the triculture on the apical surface; FIG. 2B shows an inversed configuration of FIG. 2A; and FIG. 2C shows a configuration of FIG. 2A seeded on the basolateral surface of a transwell membrane. The proposed methodology leads to a spatial arrangement that would allow for additional cellular components of the neurovascular unit to be added in the model on as needed basis;

FIG. 3A is the hCMEC/D3 monoculture representing a section of the BBB-glial vascular unit; FIG. 3B shows the hCMEC/D3 co-culture with pericytes; a partial representation of the BBB-glial vascular unit; FIG. 3C shows the hCMEC/D3 co-culture with pericytes, and FIG. 3D depicts the hCMEC/D3-triculture, which fully mimics the BBB-glial unit as it contains all physiologically relevant cell layers formed by endothelial, pericytes and astrocytes;

FIG. 4A shows that the initially seeding volume of 250 mL was used to seed astrocytes at a density of $4 \times 10^4$ cells/cm$^2$. Cells were left in the sterile hood for 30 minutes in order to settle down on the surface of the membrane. An additional 0.250 mL of astrocytes media was then added on the apical chamber where the astrocytes were seeded. The basolateral chamber was filled with 1.5 mL of astrocytes media. The astrocytes culture was then set in a sterile incubator. FIG. 4B shows that the astrocytes culture expanded and changed the morphology form round circular cells to a sharp-ended morphology at the end of 48 hrs;

FIG. 5A shows pericytes settling on a base-culture of astrocytes. Pericytes were dispersed well to avoid formation of multiple layers or overgrowth. FIG. 5B shows pericytes growing in the co-culture at the end of 48 hrs. Though the new culture looks distinct from the astrocytes culture, it was difficult to visualize a distinct layer of pericytes due to poor phase contrast in an inverted light microscope;

FIG. 6A is a micrograph showing the hCMEC/D3 cells seeded at $8 \times 10^4$ cells/cm$^2$, on top of a co-culture of pericytes & astrocytes prepared in step II. The hCMEC/D3 cells was left to grow on a base of astrocytes and pericytes for 6 days. The resulting triculture was stained on day 7 using hematoxylin. FIG. 6B shows a light micrograph of the triculture after staining;

FIG. 7A indicates that the direct-contact triculture shows more resistance to the flux of conducting ions in comparison to the mono- or co-cultures. FIG. 7B shows that the higher resistance in the triculture was confirmed using the permeability of sucrose; the triculture was less permeable in comparison to the monocultures of hCMEC/D3 alone, or co-cultures of hCMEC/D3 with astrocytes or pericytes. Note that the hCMEC/D3 monocultures served as controls and one-tailed Student's t-test was used to test statistical differences. For FIG. 7A, n=12; for FIG. 7B, n=6, and **$P<0.01$ in all of the cases;

FIG. 8A depicts that the apparent permeability of mannitol is lower in the co-culture of astrocytes and pericytes in comparison to the astrocytes or pericytes alone. FIG. 8B shows that the effective permeability of mannitol in the culture of pericytes could not be determined since it was equal to that of a free filter membrane. The effective permeability of mannitol across the co-culture of astrocytes and pericytes was lower in comparison to monoculture of astrocytes. One-tailed Student's t-test was used to determine statistical significant difference in FIG. 8B, where astrocytes monoculture served as a control, n=6, and **$P<0.01$;

FIG. 10A depicts subconfluent layer of astrocytes formed after two days (48 hrs) that shows cells with a characteristic morphology for the astrocytes. FIG. 10B depicts a sub-confluent layer of pericytes laid over the astrocytes layer at the end of two days (48 hrs) post-seeding. FIG. 10C depicts a confluent-layer of hCMEC/D3 cells laid over the underneath co-culture of astrocytes and pericytes at the end of six days post-seeding;

FIG. 11A shows a tight cell-cell junction formed between two adjacent hCMEC/D3 cells (red arrow) and a section of the cell budding off like an exosome (blue arrow). FIG. 11B shows an overlapping cell-cell junction forming minute contact points (orange arrow) and a larger nucleus occupying most of the cytoplasmic region (white arrow). FIG. 11C shows the formation of numerous vacuoles (green arrow), a large exosome (blue arrow) and a fusing cell-cell junction (orange arrow);

FIG. 12A shows wide cell-cell junctions between two adjacent pericytes (orange arrow), and a highly transparent vesicle containing granular materials in its lumen (green arrow). FIG. 12B shows an overlapping cell-cell junction between two adjacent pericytes (orange arrow), a prominent rough endoplasmic reticulum (red-pink arrow) and highly transparent exosomes (blue arrow). FIG. 12C shows a prominent nucleolus structure at the center of a pericyte nucleus (dark blue arrow);

FIG. 13A shows a stellate projection from the body center of an astrocyte (orange arrow) and a swollen body center (blue arrow). FIG. 13B shows an elongated projection from the body-center of an astrocyte. FIG. 13C shows a swollen end-section of an astrocyte (green-yellow arrow);

FIG. 14A shows two cells with similar morphologies apposed in a layered configuration; the lower cell could be a pericytes identified by a typical large transparent vesicle (green arrow) characteristic of pericytes. FIG. 14B shows tight cell-cell junctions (yellow arrow) at the top layer, which are characteristic of BMECs (or the hCMEC/D3 cells). FIG. 14C shows cell-cell connections (gap junctions, purple arrows) formed through gap spaces between two adjacent cells; such direct cell-cell contacts/gap junctions may be relevant in conveying signaling molecules between BBB cells or as novel routes for drug delivery across the BBB cell layers into the brain parenchyma;

FIG. 15A shows a multicellular structure composed of closely associated cells at the top layer, which could be endothelial (E), or pericytes (P). The middle section in FIG. 15A contains dispersed cells containing a prominent nucleus (PN); these could be disordered pericytes separated by a swollen astrocyte (A) between them. The bottom layer in FIG. 15A consists of cells lacking a prominent nucleus, or formation of vesicles; these could be astrocytes with sharp stellate ends. FIG. 15B shows a well-contrasted micrograph of the triculture model. Note that the top layer of cells formed a continuous thin membrane; this is a property of BMECs/BBB-endothelium. Also note that though certain cells in the middle section resemble endothelial cells at the top, they do not form a continuous wall; this is a property of pericytes (there is also a large nucleolus in the cells assigned as pericytes). There is a large extracellular space denoted by a double-headed arrow in the micrographs. This space could be due to the formation of excess extracellular matrix;

FIG. 16A shows junctional contacts between two endothelial cells (red arrow), and a high population of vacuoles (green) in the two adjacent endothelial cells. The middle and basal layers in panel (A) show prominent mitochondria characteristic of astrocytes at the BBB in vivo (maroon arrow). FIG. 16B shows middle and basal layers containing cells with prominently large nucleus and nucleolus (dark blue arrow). Cells in the basal layer of FIG. 16B formed widened cell-cell junctions (white arrow). FIG. 16C shows cells that form a continuous cell layer (characteristic of BMECs, see red arrow) at the top layer, a cell in the middle layer that lacks connections with adjacent cells (a characteristic of pericytes) and a basal layer of cells that have long sharp projections, lacking prominent vesicles (a characteristic of astrocytes);

FIG. 23A shows hydrocortisone added to media at 1.4 µM or 100 nM at the start of hCMEC/D3 plating or two days post plating. FIG. 23B shows lithium chloride at 10 mM compared to control (0 mM) when added at the start of hCMEC/D3 plating or two days post plating. FIG. 23C shows HEPES concentrations of 10 mM, 25 mM, and 50 mM added to media for hCMEC/D3 monolayer in comparison to direct culture. Studies shown in FIGS. 23A~23C were run in triplicate and subjected to student's T-Test and Mann-Whitney test (23A and 23C) or one-way ANOVA with Bonferroni post-hoc test or Kruskal-Wallis with Dunn's post-hoc test (23B). Significant changes are noted with an asterisk (*) for p<0.05 and (**) for p<0.01. Significant levels are reported as (t-test, MW) or (one-way ANOVA, KW). Error bars represent 1 standard deviation (n=3);

FIG. 25 shows a chart of apparent permeability of [$^{14}$C]-Inulin, a paracellular marker, across the direct contact coculture. Studies were subjected to one-way ANOVA with a Bonferroni post hoc test and Kruskal-Wallis with Dunn's post-hoc test. Significant changes are noted with an asterisk (*) for p<0.05 and (**) for p<0.01. Significant levels are reported as (one-way ANOVA, KW). Error bars represent 1 standard deviation (n=6);

FIG. 26 shows the apparent permeability of [$^{14}$C]-Mannitol and [$^{14}$C]-Sucrose across direct and indirect contact cocultures. Studies were run in triplicate and subjected to student's T-Test or Mann-Whitney test. Significant changes are noted with an asterisk (*) for p<0.05 and (**) for p<0.01. Significant levels are reported as (t-test, MW). Error bars represent 1 standard deviation (n=3);

FIG. 27 shows a chart of the apparent permeability of [$^{14}$C]-Propanolol, a passive transcellular permeability marker. Studies were subjected to one-way ANOVA with a Bonferroni post hoc test and Kruskal-Wallis with Dunn's post-hoc test. Non-significant changes (p>0.05) were seen between monoculture and coculture. Error bars represent 1 standard deviation (n=3)

Figure 1:
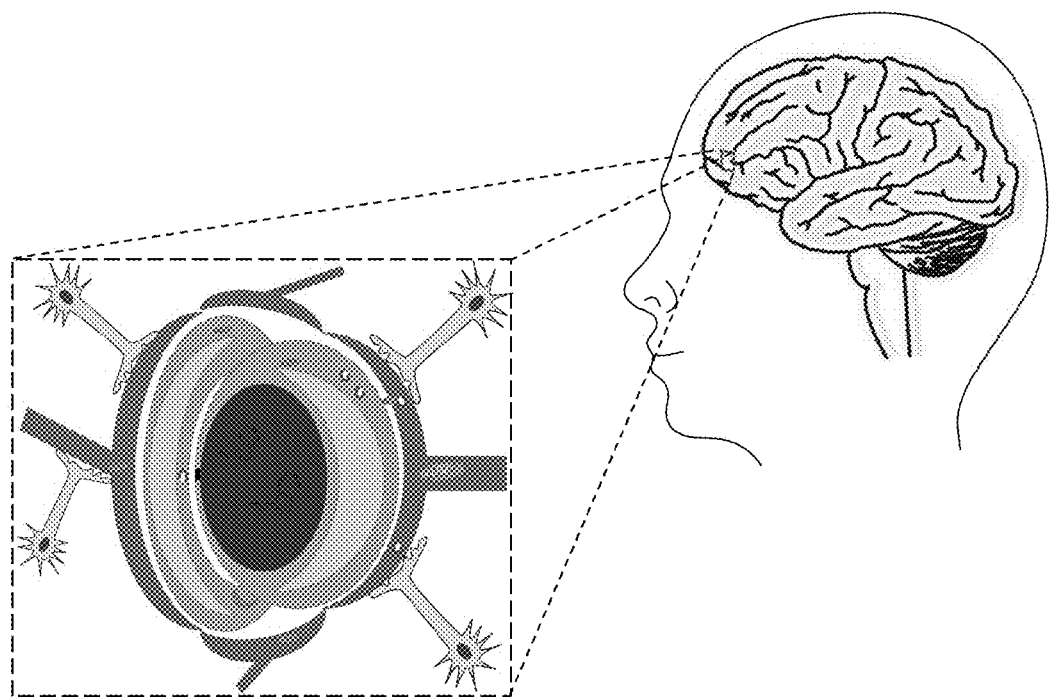
FIG. 1 shows a neuroprotective BBB-system. The bright green arrow shows a neuron (N), the light blue arrow shows an astrocyte (A), the black arrow shows a pericytes (P) and the purple arrow shows a BBB-endothelium. Note that for a neuronal drug delivery to be attained, a drug molecule would have to be transported past the BBB-endothelium, the extracellular matrix, and pericytes or astrocytes. Cell-cell junctions (molecular channels) that connect neurons, astrocytes, pericytes and the BBB-endothelium may provide an alternative transport pathway to circumvent tight junctions, extracellular enzymes, and CFS clearance in neuronal drug delivery. An in vitro-multicellular model of the BBB that allows for unlimited and direct interactions between the cellular constituents of the BBB-glial unit would be useful in preclinical CNS-drug delivery studies.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This present disclosure relates to a direct-contact coculture and a triculture systems that are useful for studying the blood brain barrier (BBB). This direct-contact coculture and triculture systems exhibits a more physiologically representative configuration of the BBB-system in vivo. We have developed a triculture model of the BBB on the apical surface of a transwell chamber in a way that allows all the principal cellular components of the BBB-system to interact as they would do in their native in vivo environment, where brain microvessel endothelial capillaries are completely enwrapped by the astrocytes and partly by pericytes. The apical triculture system can be used to study the functions of BBB, and to predict the effectiveness of a novel drug candidate on its entry into the brain parenchyma.

In a parallel manner, a coculture model for the BBB on the apical surface of a Transwell system using BMECs and astrocytes is disclosed. The coculture system better mimics the BBB in neurological conditions in which pericytes may be lost from the BBB-system as it is the case of neurodegenerative disorders. In addition, pericytes tend to be lost with aging. Thus a coculture system may be more physiologically relevant for predicting drug transport across the BBB or neurotoxicity related to BBB-dysfunctions.

In some aspects, the present invention relates to a process of plating multiple cell types of the neurovascular unit in direct contact with one another, useful to study various aspects of the BBB as it pertains to drug screening, drug delivery, drug efficacy and toxicity, etc.

In some other aspects, the present invention relates to a process of plating multiple cell types in direct contact of coculture and triculture model systems with some representative cell type variations, including:
  a. The use of cells derived from different species (e.g. human, porcine, bovine, etc.);
  b. The use of cells types that are immortalized, primary, stem cell derived, or otherwise modified; and
  c. The use of cells from normal or diseased origin or otherwise modified to reflect a diseased state.

In some aspect, the present invention relates to a process of plating multiple cell types on a cell culture surface or support that those cells are in direct contact on the apical or basolateral surface of a permeable filter support, cell culture well plate, glass slide, or any other surface commonly used for cell culturing purposes.

The present disclosure also includes a novel method of use for an in vitro triculture BBB model that can be utilized for drug discovery and drug delivery screening efforts. The compositional properties of the model allow for either primary or proliferative astrocytes, pericytes, and BMECs to be cultured on the apical surface of a Transwell® chamber to form direct-contact interactions, which in some embodiments may be referred to as layers. The cell types may be collected from different species or origin in order to provide optimized conditions specific to the outcomes desired. In addition, the potential to perform assays where the triculture permeability can be linked to neuronal or other brain cell response can be monitored.

The innovation in the model disclosed herein lies in the unique configuration that the cells are cultured comparative to traditional triculture blood brain barrier in vitro methods. Briefly, approach disclosed herein enables a direct interaction of principal cellular components of the BBB system, namely supporting cells of the BBB, such as the astrocytes and pericytes, and BMECs cultured in optimized extracellular matrices (ECM) directly applied as a reagent and/or produced by the three cell types during the course of triculture growth. After the desired astrocyte and pericyte layer growth is reached, a source of BMECs at pre-optimized densities can be added and cultured to the desired level of confluency required to reach experimental goals. Here again, the layer of BMECs can be seeded on top of the supporting cells in the absence or presence of ECM substrates in order to reach the desired experimental properties and to form an optimized, physiologically relevant triculture BBB model.

Moreover, since pericytes and astrocytes may be found in capillaries perfusing other tissues within the body, the use of peripheral endothelial cells could be cultured in an analogous manner to study tissue specific outcomes. Another key feature is that primary cells may be collected and cultured from patients or animals of differing ages to assess the effects of ontogeny on permeation or neuronal cells.

The present disclosure therefore includes disclosure of at least the following:

1) Apical and "direct-contact" triculture methodology
2) Utility of the methods in drug discovery (small molecule, large molecule and biotechnology derived compounds), either in high through put or high content screening studies
3) Utility of the methods in studying the transport properties of small and macromolecule (substrate) permeation across the BBB system
4) Utility of the methods in the role of BBB system substrate permeation on resultant neurotoxicity
5) Utility of the methods in modeling the role of BBB system substrate permeation in the mitigation of neurological diseases, e.g. Alzheimer primary BMECs, derived neurons or cancer cell lines derived from the brain.
6) Utility of the methods in studying ontogeny of the BBB system utilizing primary or transformed cells derived from different age populations.
7) Utility of the methods in evaluating drug delivery strategies to the brain
8) Utility of the methods of inducing stem cell populations to reflect the BBB upon triculture.
9) Utility of a similar approach to mimic perfusion across systemic endothelial cell populations with astrocytes and/or peripheral pericytes.
10) Developing high throughput screening approaches for rapid screening of BBB penetration, efficacy, and/or neurotoxicity
11) Modifying cell densities, media additives, and culture conditions to tailor the BBB triculture function to observe desired effects, e.g. increased transporter expression, increased tightness, etc.
12) Utilizing primary or proliferative cell lines derived from different species to either mimic human BBB penetration or to identify factors that may be critical for extrapolation of in vitro and in vivo species specific results to humans.
13) The utility of the co-culture model as a surrogate to delineate differences that may occur in aging or in diseases where either the pericyte or astrocyte densities may change. This may be applied as an alternative model to study all of the properties mentioned in the other claims.

A person of ordinary skill in the art may carry out plating the cells in direct contact at any reasonable cell density or with any variation of extra cellular matrix conditioning. For example, the cell seeding densities may be optimized differently for individual type and origin of a cell line according to the method disclosed herein. The amount of extracellular matrix that is used may be varied and optimized for the particular cell types being used. Additionally, variation of the overall density or confluency of each cell line may be manipulated to mimic a specific disease state.

In some illustrative embodiments, the present invention relates to a method for preparing a cell culture system comprising the steps of:
  a) preparing a cell culture plate with a permeable membrane support;
  b) seeding a first cell line on said membrane support and proliferating said first cell line for about 2 days in the presence of a cell culture medium;
  c) removing said cell culture medium and washing proliferated cells of said first cell line;
  d) seeding a second cell line over proliferated cells of said first cell line;
  e) proliferating said second cell line and first cell line in the presence of cell culture medium; and
  f) replacing cell culture medium every other day until proliferated cells reach confluency as determined by stabilized normalized Transendothelial Electrical Resistance (TEER) or by other established methods of assessing cell proliferation or differentiation.

In some other illustrative embodiments, the present invention relates to a method for preparing a cell culture system disclosed herein further comprising a step of: seeding a third cell line over the proliferated cells of said first cell line and proliferating said third cell line for about 2 days in the presence of a culture medium before seeding the second cell line.

In some other illustrative embodiments, the present invention relates to a method for preparing a cell culture system, wherein said third cell line is pericytes.

In some other illustrative embodiments, the present invention relates to a method for preparing a cell culture system, wherein said first cell line is astrocytes or other glial cells, said second cell line is brain microvessel endothelial cells (BMECs) of human or animal origin, primary, immortalized, normal or in a diseased state, or Human Brain Endothelial Cells (HBECs), and said third cell line is pericytes.

In some other illustrative embodiments, the present invention relates to a method to determine or predict drug delivery efficacy and/or toxicity of a drug candidate using a cell culture system prepared according to the process disclosed herein.

In some illustrative embodiments, the present invention relates to a cell culture system prepared according to the process disclosed herein.

In some other illustrative embodiments, the present invention relates to a cell culture system prepared according to the process disclosed herein, wherein said first cell line is astrocytes or other glial cells and said second cell line is BMECs of human or animal origin, primary, immortalized, normal or in a diseased state, or HBECs.

In some other illustrative embodiments, the present invention relates to a cell culture system prepared according to the process disclosed herein, wherein said second cell line is proliferative human derived cerebral microvessel endothelial cells hCMEC/D3.

In some other illustrative embodiments, the present invention relates to a cell culture system prepared according to the process disclosed herein, wherein said second cell line is preprogrammed induced pluripotent stem cells.

In some illustrative embodiments, the present invention relates to a method for preparing a cell culture system, wherein said first cell line is astrocytes or other glial cells.

In some other illustrative embodiments, the present invention relates to a method for preparing a cell culture system, wherein said second cell line is BMECs of human or animal origin, primary, immortalized, normal or in a diseased state, or HBECs.

In some other illustrative embodiments, the present invention relates to a method for preparing a cell culture system, wherein said first cell line is astrocytes or other glial cells and said second cell line is BMECs of human or animal origin, primary, immortalized, normal or in a diseased state, or HBECs.

In some other illustrative embodiments, the present invention relates to a method for preparing a cell culture system, wherein said astrocytes or other glial cells and BMECs of human or animal origin, primary, immortalized, normal or in a diseased state, or HBECs are both seeded on the same side of a cell culture surface and are in direct contact.

In some other illustrative embodiments, the present invention relates to a method for preparing a cell culture system, wherein said second cell line is proliferative human derived cerebral microvessel endothelial cells hCMEC/D3.

In some other illustrative embodiments, the present invention relates to a method for preparing a cell culture system, wherein said second cell line is preprogrammed induced pluripotent stem cells.

In some illustrative embodiments, the present invention relates to a method to determine or predict drug delivery efficacy and/or toxicity of a drug candidate using a cell culture system prepared according to the process disclosed herein.

In some other illustrative embodiments, the present invention relates to a method for preparing a cell culture system, wherein said permeable membrane support or cell culture surface is pre-conditioned with poly-L-lysine or other selected extra cellular matrix overnight before plating said first cell line.

In some other illustrative embodiments, the present invention relates to a method for preparing a cell culture system, wherein said cell culture medium is a buffered medium comprising fetal bovine serum, penicillin streptomycin, and necessary growth factors.

In some other illustrative embodiments, the present invention relates to a cell culture system prepared according to the method, wherein said first cell line is astrocytes or other glial cells and said second cell line is BMECs of human or animal origin, primary, immortalized, normal or in a diseased state, or HBECs.

In some other illustrative embodiments, the present invention relates to a method for preparing a cell culture system, wherein said second cell line is preprogrammed induced pluripotent stem cells.

In some other illustrative embodiments, the present invention relates to a method for preparing a cell culture system, wherein said second cell line is proliferative human derived cerebral microvessel endothelial cells hCMEC/D3.

In some other illustrative embodiments, the present invention relates to a cell culture system prepared according to the steps of:
  a. preparing a cell culture plate with a permeable membrane support;
  b. seeding astrocytes or other glial cells on said membrane support and proliferating said astrocytes or other glial cells for about 2 days in the presence of a cell culture medium;
  c. removing said cell culture medium and washing proliferated astrocytes or other glial cells;
  d. seeding pericytes over said astrocytes or other glial cells and proliferating said pericytes for about 2 days in the presence of a cell culture medium;
  e. removing said cell culture medium and washing proliferated pericytes;
  f. seeding brain microvessel endothelial cells (BMECs) of human or animal origin, primary, immortalized, normal or in a diseased state, over said pericytes and astrocytes or other glial cells;
  g. proliferating said BMECs, pericytes, and astrocytes or other glial cells in the presence of cell culture medium; and
  h. replacing cell culture medium every other day until the cells reach confluency as determined by stabilized normalized Transendothelial Electrical Resistance (TEER) significantly greater than that of a BMEC monoculture or by other established methods of assessing proliferation or differentiation.

CNS barriers include BBB endothelium, the tight junctions at arachnoid epithelium, and the arachnoid plexus epithelium forming the Blood-CSF barrier. BBB capillary length within the body is ~650 km and is not fenestrated. Mainly receptor-mediated pinocytosis exists, and complex tight junctions prevent the entry of large polar molecules into the brain. (Smith and Gumbleton, *J. Drug Target*, 2006, 14(4): 191-214). Astrocytic end feet cover >99% of the BBB endothelium, and pericytes cover approximately 20% of the microvascular circumference (Armulik, Genove et al. *Nature*, 2010, 468: 557-561). The basal lamina extracellular matrices (ECM) is composed of laminin, fibronectin, tenascin, collagens and proteoglycans.

Astrocytes and other glial cells. Glial cells, or otherwise known as neuroglia, are found throughout the central nervous system (CNS) and neurovascular unit (NVU). These cells are responsible for secreting factors that maintain the CNS and the blood-brain barrier (BBB). Glial cells include astrocytes, microglia, and oligodendrocytes. The role of astrocytes in the BBB has been well established as a cell that secretes soluble factors that modulate the phenotype of the BBB (Abbott, Ronnback et al. *Nature Reviews Neuroscience* 2006, 7(1): 41-53). Though the presence and role of astrocytes is most predominant in the BBB compared to other glial cells, these additional cell types are known to play a role in BBB maintenance and development. For example, oligodendrocytes are known to secrete soluble factors that support BBB integrity, while microglia have been shown to become active in brain injury or trauma (Watzlawik, Warrington et al., *Exp Rev Neurotherapeutics* 2010, 10(3): 441-457). The use of astrocytes in the disclosed direct contact co- and triculture models would represent one state of the BBB. The addition of other glial cells, or the replacement of astrocytes with oligodendrocytes or microglial, in the direct contact models would be representative of another state of the BBB (e.g. brain injury, brain trauma, onset of neurodegenerative disease, etc.).

BMECs vs. HBECs. Brain microvascular endothelial cells (BMECs) is the cell line most responsible for the formation of the blood-brain barrier (BBB) by forming restrictive tight junctions and expressing highly active efflux transports to prevent the permeation of xenobiotics into the brain. BMEC is most commonly used to refer to the endothelial cells that make up the BBB, there is a wide variety of endothelial cell lines that can be categorized as a type of BMEC. Human BMECs (HBEMCs) is a further classification of BMECs to those of human origin. Human brain endothelial cells (HBECs) is an additional way of classifying BMECs that are of human origin, and is often used interchangeable with HBMECs.

Types of BMECs. The breadth of BMECs use in in vitro models of the BBB is extensive. Cell lines can vary by species origin, proliferative state (primary cells taken from cadaver versus immortalized cell lines that have been transfected to express a phenotype through repeated culturing), cells derived from stem cells, and disease state (e.g. primary cells taken from cadaver patients having Alzheimer's or Parkinson's Disease). Helms et al. has extensively reviewed the various cell models that have been used for in vitro modeling of the BBB, which have included primary and immortalized cells from different species (e.g. murine, porcine, bovine, and human) and cells generated from human stem cells (Helms, H. C., et al., *J. Cerebral Blood Flow Metabolism*, 2016, 36(5): 862-890). The practice of isolating primary BMECs for their use in in vitro BBB models is well established for animal and human cell lines (Navone, S. E. et al., *Nat Protoc* 2013, 8(9): 1680-1693). By using this method, a person familiar with the field could isolate BMECs from various human cadaver sources to mimic a particular disease or age state of the BBB when used in the direct contact models. Table 1 below lists some examples of BMECs that are commonly used for in vitro BBB models and could be readily utilized in the direct contact model (Helms, H. C., et al., *J. Cerebral Blood Flow Metabolism*, 2016, 36(5): 862-890; Weksler, B. et al., *Fluids Barriers CNS*. 2013, 10:16).

TABLE 1

Example BMEC cell lines use for BBB in vitro models.

| Cell Line | Origin and Proliferative State |
|---|---|
| hCMEC/D3 | Human Immortalized |
| BB19 | Human Immortalized |
| HCEC | Human Immortalized |
| HBEC-5i | Human Immortalized |
| NKIM-6 | Human Immortalized |
| HBMEC-3 | Human Immortalized |
| TY08 | Human Immortalized |
| HBMEC/ciβ | Human Immortalized |
| cEND and cereBEND | Mouse Immortalized |
| Primary mouse BMEC | Mouse Primary |
| Primary bovine BMEC | Bovine Primary |
| Primary porcine BMEC | Porcine Primary |
| hiPSC derived BMEC | Human derived from pluripotent stem cells |

There are several challenges for CNS drug development, as data shows that significant attrition occurs with only 6.2% of all clinically tested lead candidates designed to mitigate CNS disorders approved. Higher attrition rates are incurred with agents for neurological disorders, and translation of approved CNS agents require approximately 18 years. Increasing incidents of neurological disorders have led to a significant need for a better approach in preclinical screening. Representative causes for attrition include:
 a) preclinical evaluation fails to accurately predict in vivo performance;
 b) poor efficacy and high toxicity are often clinically observed with neurotherapeutics;
 c) restrictive physiological barriers minimize effective drug delivery to the brain;
 d) prior art in vivo models for the BBB permeation lack in vivo physiological similarity;
 e) toxicity evaluation for approving neurotherapeutic agents have become more stringent.

Initial studies referenced herein entailed the selection of optimal seeding densities for the three types of cells with a desirable and predictable trend in the Transendothelial Electrical Resistance (TEER). Since TEER measurements are solely based on the mobility of ions across the triculture system, the TEER method was simply used as a guide to probe the stability of the triculture systems obtained from various cell-seeding density ratios. The tightness of the selected BBB system was then investigated using sucrose and mannitol (common markers for paracellular permeability). The initial results indicated that modeling the BBB system in a "direct contact" coculture or triculture system leads to lower effective paracellular permeability values in comparison to the monoculture of BMECs. The interaction of pericytes with endothelial cells and astrocytes was also investigated, and according to initial results, brain vascular pericytes can induce the BBB effect on endothelial cells in a coculture system in a similar manner to the astrocytes. In addition, interaction of pericytes and astrocytes in a "direct contact" coculture also led to a significant reduction in the paracellular permeability of paracellular markers. Such induction of the BBB property in the astrocytes may be indicative of additional barrier junctions at the astrocytes layer (astrocytes are known to express occludin, a protein associated with tight junctions), for example. This is largely seen only in undifferentiated astrocytes.

Cell Seeding

In order to establish a triculture model of the BBB, a determination of cell seeding density ratios of BMECs to pericytes and astrocytes that would provide significantly increased resistance comparative to the monoculture as observed by TEER was sought. Therefore, TEER trends corresponding to various seeding density ratios were evaluated, and the seeding density ratio was selected based on stability in the TEER trend upon achieving a statistically significant steady state increase in electrical resistance. The methodology is described below.

Briefly, and by way of example, Corning Transwells® (polyester clear 3460, 12 well format) were first incubated with poly-1-lysine (PLL) for 30 minutes. Excess PLL solution was then removed by aspiration, and differing seeding densities of primary astrocytes (ScienCell Research) were plated and cultured on the apical side of the filter support until they reached confluency by visualization under an inverted microscope (two days later) in recommended astrocyte media. Prior to seeding primary pericytes (ScienCell Research) onto the astrocytes monoculture, the astrocyte conditioned media was aspirated and the cells were washed 2× with sterile Phosphate Buffered Saline (PBS; pH 7.4) solution. Next, PLL was added on top of the astrocytes for approximately 15 minutes. Excess PLL was then removed and differing densities of pericytes were plated onto the astrocytes monolayer. The co-culture was maintained with recommended pericyte media on the apical side and astrocyte media on the basolateral side for two days. Before plating BMECs onto the direct co-culture, the media is aspirated and the co-culture was washed 2× with PBS and incubated with rat tail collagen type I for 15 minutes. Excess collagen was removed and then the different seeding densities of the BMECs were plated onto the co-culture to form a direct tri-culture configuration. The triculture was then maintained under endothelial cell media (EBM-2) on the apical side and astrocyte media on the basolateral side.

TEER values were recorded and plotted from day one after setting up the triculture system. Initial results for TEER trends are indicated in figures below. Based on these observed trends, a seeding ratio of $(40A:40P:80B) \times 10^3$ cells/cm$^2$ was selected, where A stands for astrocytes, P stands for pericytes, and B for the BMECs (hCMEC/D3 cells where used in the initial studies). Other ratios may be selected and can also result in human BBB physiologically relevant model (Table 2). These seeding densities will vary based upon the cell type or desired features to be represented in the direct contact model.

TABLE 2

Cell Seeding Ratios and Triculture Stability

| Seeding ratio × 1000 cells/cm$^2$ | Maximum Raw TEER (ohm-cm$^2$) | Days for stable TEER |
|---|---|---|
| 40A:40P:100E | 207 ± 4 | 7 |
| 50A:50P:100E | 211 ± 1 | 7 |
| 50A:50P:80E | 196 ± 1 | 7-9 |
| 40A:40P:80E | 201 ± 5 | 5-9 |

As an improvement on this model and form of further validation, preprogrammed induced pluripotent stem cells were used as BMEC cells seeded on top of astrocytes and pericytes. The same culture methods as stated above were used and showed that stem cells are another option for an endothelial cell line with continued optimization. TEER and permeability data shows that stem cells are yet another viable option for the use of this culturing method when plated as a coculture or a triculture.

Permeability Studies

Radiolabeled paracellular markers were used to determine the tightness of the paracellular junctional complexes to compounds that are closer in size to actual small molecule therapeutic agents. Upon establishing a TEER trend indicating stability, permeability studies with sucrose and mannitol were conducted. For the 40A:40P:80B out on day 4, 5, 6, 7 and 8 after the hCMEC/D3 cells were seeded. Prior to the permeability measurements, the triculture was washed 2× with PBS and then incubated with HBSS (0.5 mL on the apical and 1.5 mL on the basolateral) for about 20 minutes at 37° C. During the 20 min incubation, a solution of the paracellular marker was prepared at a concentration of 0.25 μCi/mL to make a stock solution. After 20 minutes, the HBSS was aspirated from the Transwell®, the filter was then transferred to a new well containing 1.5 mL of HBSS and then 0.5 ml of radiolabeled stock solution was added to the apical side of the triculture to begin the permeability study. The study was conducted on a rocking platform inside a 37° C. incubator. Basolateral (receiver) samples are collected at 15, 30, 45, 60 and 90 minutes to calculate the rate of transfer of [C-14]-sucrose or [C-14]-mannitol across the triculture system. The apical (donor) solution was also sampled at 90 minutes to account for mass balance.

The permeability coefficients were then calculated from receiver appearance kinetics using Equations 1 and 2:

$$P_{app} = \frac{\Delta M / \Delta t}{A \times C_i \times 60} \left(\frac{cm}{s}\right) \quad \text{Eq. (1)}$$

$$\frac{1}{P_{app}} = \frac{1}{P_e} + \frac{1}{P_t} \quad \text{Eq. (2)}$$

where $P_{app}$ stands for apparent permeability, $\Delta M/\Delta t$ is the rate of mass transfer of a marker molecule from the apical side of the transwell filter support to the basolateral side, A is the area onto which the cell culture is grown, $C_i$ is the initial concentration of the marker molecule on the apical side, $P_e$ is the effective permeability coefficient, and $P_t$ is the permeability of the marker across the transwell void of any cell culture. The rest of the symbols carry their usual meanings. Initial studies suggested that day 6 post triculture seeding would be the optimal day at a seeding density ratio of (40A:40P:80B)×$10^3$ cells/cm$^2$ in this exemplary study.

Comparing Triculture, Coculture and Monoculture Systems

Comparison of paracellular permeability coefficients between "direct contact" triculture, cocultures of astrocytes or pericytes with endothelial cells, and endothelial monocultures was performed. When seeding cocultures, a seeding density of (40A:80B)×$10^3$ cells/cm$^2$ in the astrocytes coculture and (40P:80B)×$10^3$ cells/cm$^2$ in the case of pericytes coculture. This comparative study shows that the triculture and coculture systems have similar effect in reducing the paracellular permeability.

Figure 22A:
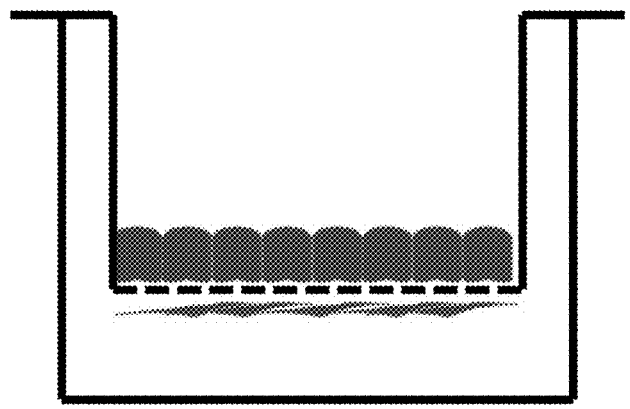
FIG. 22A depicts previous direct contact coculture model with BBEC and astrocytes separated by Transwell® permeable filter support.
Figure 22B:
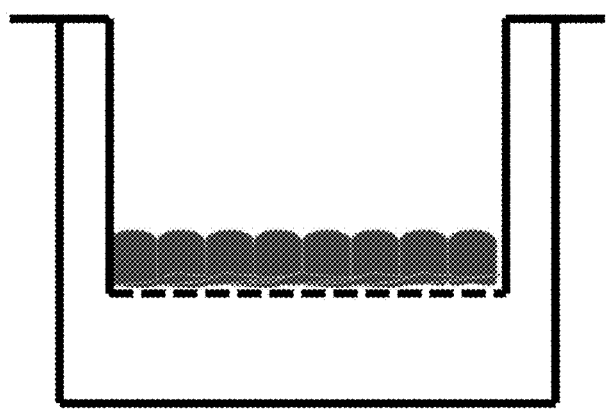
FIG. 22B depicts the direct contact coculture model disclosed herein, with BBEC and astrocytes in direct cell-cell contact. BBEC and astrocytes depicted in red and purple respectively.

Currently there are different representative cell configurations utilized in the medical arts for in vitro blood brain barrier screening purposes. While some of these models are considered "direct contact", note that there exists a physical filter barrier in between the cell layers. (Hatherell, Couraud et al. 2011) FIGS. 22A and 22B show the direct comparison of the cell culture system (coculture) with the known cell culture system. FIGS. 22A and 22B depict past (indirect) vs. current direct contact coculture models. FIG. 22A shows a previous direct contact coculture model with BBEC (upper cells) and astrocytes (lower cells) separated by Transwell® permeable filter support. FIG. 22B shows a direct contact coculture model disclosed herein, with BBEC and astrocytes in direct cell-cell contact.

One of the most often used immortalized human BMEC cell lines is the human cerebral microvessel endothelial (hCMEC/D3) cell line. The hCMEC/D3 cell line was established through hTERT and SV40 large T antigen immortalization of endothelial cells isolated from microvessels of a human temporal lobe. (Weksler, Subileau et al. 2005) The hCMEC/D3 cultures form monolayers on collagen-coated surfaces and are contact inhibited lending themselves to high throughput Transwell® permeation studies. Analysis of the cell line and has shown similarities in morphology and protein expression between hCMEC/D3s and primary human BMECs. However, hCMEC/D3s do not appear to form restrictive tight junctions consistent with those found in vivo, reaching TEER values of only 30-50 Ω*cm$^2$ compared to TEER values of over 1000 Ω*cm$^2$ in vivo in other species including the frog (Weksler, B., et al., *Fluids Barriers CNS*, 2013, 10: 16). These leaky tight junctions may allow paracellular movement of compounds that permeate by the transcellular route in vivo, leading to irrelevant permeability values. While optimization of culture conditions, e.g. media, density, cell source, etc., has led to modest increases in monoculture TEER, these values are still well below those seen in vivo (Hatherell, K. et al., *J. Neurosci Methods*, 2011, 199(2): 223-229).

Due to the leakiness of these monocultures, many groups have examined methods for reducing the paracellular permeability of these models. One approach is to use astrocyte conditioned media (Siddharthan, V. et al., *Brain Res.* 2007, 1147: 39-50). In these studies, soluble factors released by the astrocytes were able to interact with BMECs to create a more in vivo-like environment that lead to enhanced differentiation and reduced paracellular permeability. However, for hCMEC/D3 cultures, non-significant changes were seen in TEER when using astrocyte conditioned media (Eigenmann, D. et al., *Fluids Barriers CNS*, 2013, 10(1): 33). Instead, the most significant reductions in paracellular permeability were seen when astrocytes were grown on the basolateral side of the filter or on the plastic well surface in the same Transwell® as the hCMEC/D3s (as shown in FIG. 22A) (Weksler, B., et al., *Fluids Barriers CNS*, 2013, 10: 16). While a reduction in paracellular permeability of marker compounds and increases in TEER were seen for both of these conditions, greater changes were observed in cells grown on the basolateral side of the Transwell®. These models are likely more physiologically relevant due to the symbiotic signaling and differentiation that is able to occur when both cell types are grown in the same culture. In addition, the increased tightness seen when growing astrocytes on the basolateral side of the Transwell® may reflect a closer proximity of astrocytic-released factors to endothelial cells thus producing a greater response through reduced dilution. Moreover, it is thought that the model in which cells are grown on the bottom of the Transwell® permeable support may lead to tighter junctions due to the ability of the astrocytic endfeet to migrate through the pores of the filter and interact with the BMECs through direct contact. However, it should be noted, that migration through Transwell® supports, especially through 0.4 μm pores which best support endothelial cell culture, is infrequent (Garcia, C. M., et al., *Developmental Brain Res* 2004, 152(1): 25-38).

It is understood that the interplay between BMECs and astrocytes may serve an important role in differentiation of BMECs into providing a BBB phenotype. In addition, these studies have shown the proximity of the astrocytes and BMECs may be crucial (Garcia, C. M., et al., *Developmental Brain Res* 2004, 152(1): 25-38). However, the methods described in previous coculture models entails separating BMECs and astrocytes by a filter support and in most cases an extracellular matrix. While the Transwell® support is often depicted to be thin in cartoon representations, the support is approximately 10 μm thick and may represent a significant barrier to cell-cell interactions.

As referenced herein, the present disclosure provides information supporting the notion that removing this obstruction and allowing direct cell-cell contact can better enable direct symbiotic signaling and differentiation to occur, which in turn can lead to further reduction in paracellular permeability and a more in vivo relevant model. An illustration of the model is shown in FIG. 22B and referenced in further detail herein. The present disclosure provides evidence that direct contact triculture system may provide additional benefits to the coculture tightness and physiological relevance.

FIG. 1 depicts a representation of the neurovascular unit as it is found in the body. The premise of the direct contact coculture and triculture models disclosed herein, is to mimic the arrangement of the cells of the neurovascular unit in a cellular model.

Figure 2A:
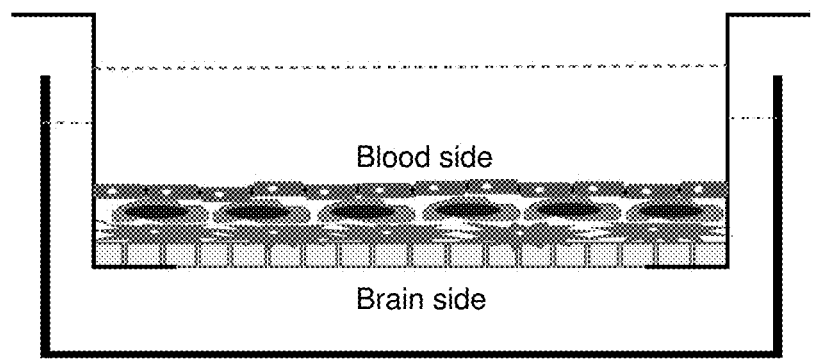
FIGS. 2A~2C depict a direct-contact triculture methodology for mimicking the BBB-glial unit on a Transwell® support.
Figure 2B:
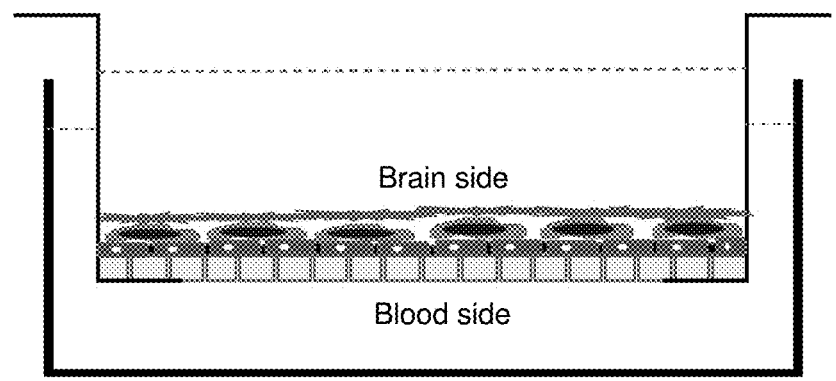
Figure 2C:
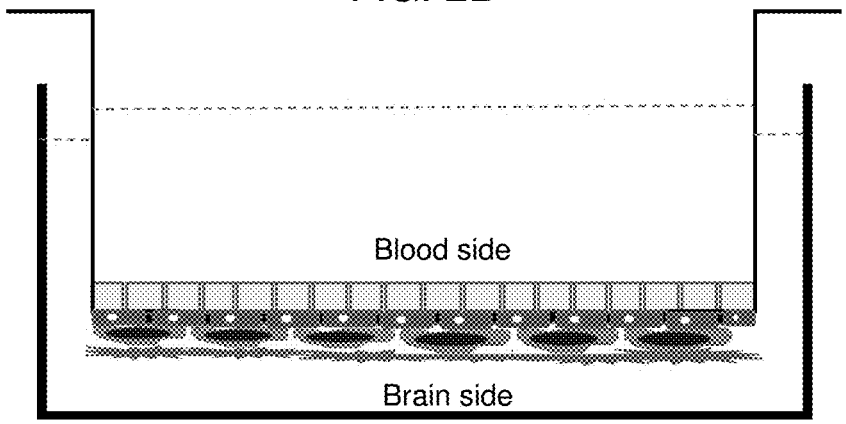

FIG. 2A depicts a representative cell configuration of the present disclosure. Various routes of permeation are shown therein, including influx transporter mediated permeation, passive transcellular permeation, passive transcellular and efflux permeation, passive paracellular permeation, metabolism, and efflux of the metabolites. BMECs are depicted within FIG. 2A as being on top of astrocytes and pericytes in triculture. In such an in vitro model (consistent with the in vivo BBB), BMECs are on top of pericytes and astrocytes to form the restrictive BBB. The bottom well, if desired, could include neurons, potentially derived or mimicking healthy and diseased states, so to study desired neurotoxicity and/or neuroactivity. FIG. 2A shows a simplified schematic of the triculture system disclosed in this invention. FIGS. 2B and 2C depict the direct contact triculture model as it could be used in alternating cell seeding patterns or on the basolateral side of a filter support.

Figure 3A:
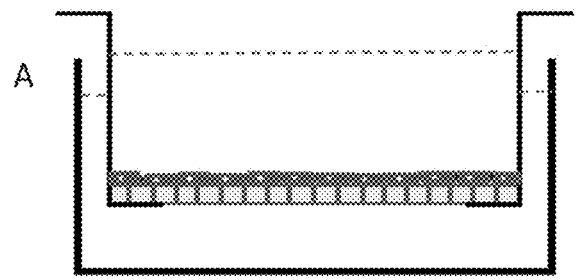
FIGS. 3A~3D show BBB-culture models examined in current studies.
Figure 3B:
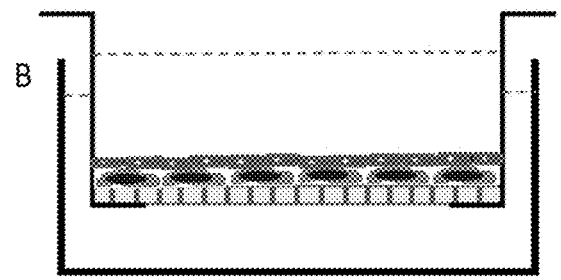
Figure 3C:
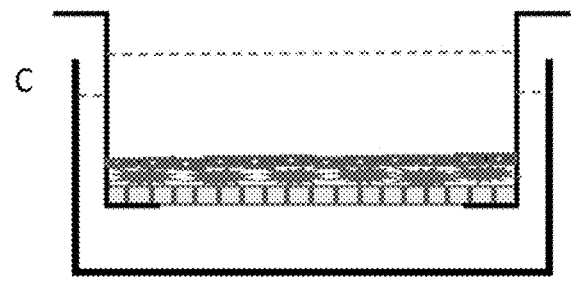
Figure 3D:
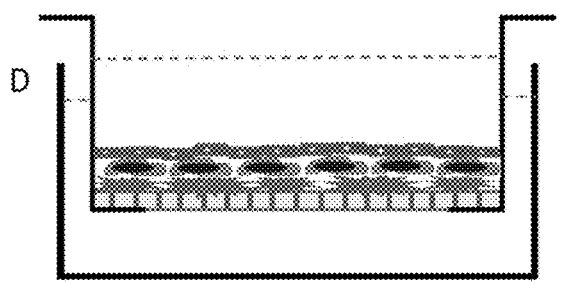

FIGS. 3A~3D show a schematic representation of the BBB culture models that are used in the studies that are disclosed. FIG. 3B depicts the direct contact coculture model utilizing astrocytes and BMECs. FIG. 3D depicts the direct contact triculture model utilizing astrocytes, pericytes, and BMECs.

Figure 4A:
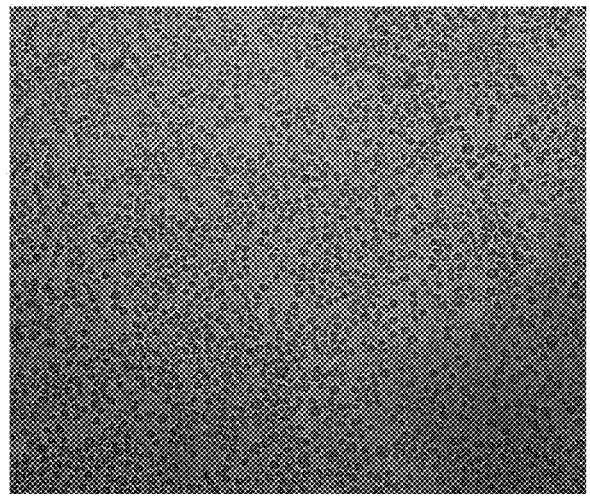
FIGS. 4A~4B show the preparation of a layer of astrocytes in the course of seeding a direct-contact triculture. Prior to seeding, the suspended astrocytes were sheared up and down using a Pasteur pipette to ensure that no cell clumps were seeded on the transwell membrane.
Figure 4B:
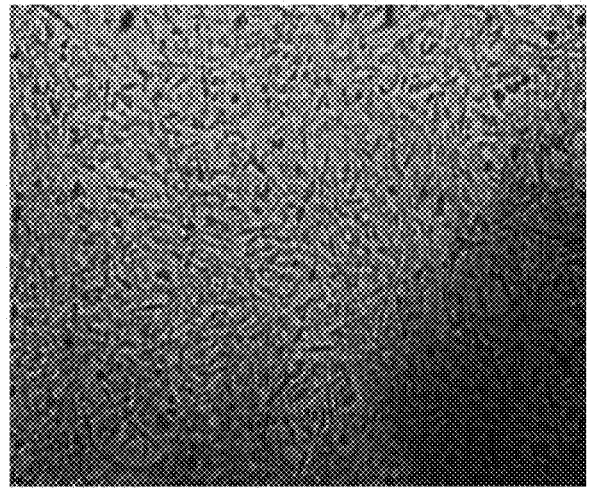

FIG. 4A depicts the morphology and density of astrocytes upon initial plating of the cells on a preconditioned surface. FIG. 4B depicts the morphology of the astrocytes after the cells have proliferated for 48 hours.

Figure 5A:
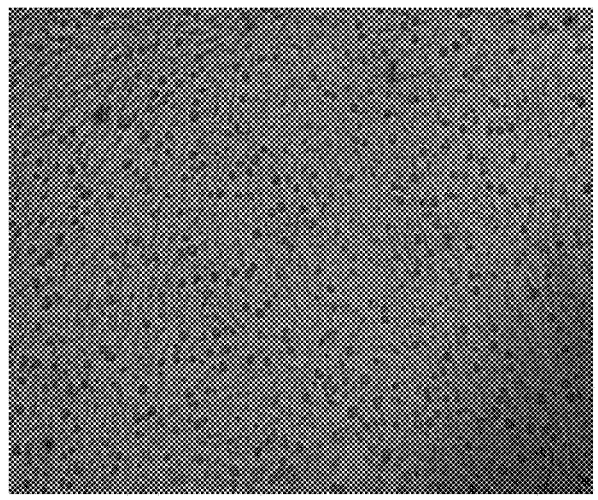
FIGS. 5A~5B show the culturing a direct layer of pericytes on top of the astrocytes prepared in step I. Pericytes were prepared in the same way as astrocytes in step I.
Figure 5B:
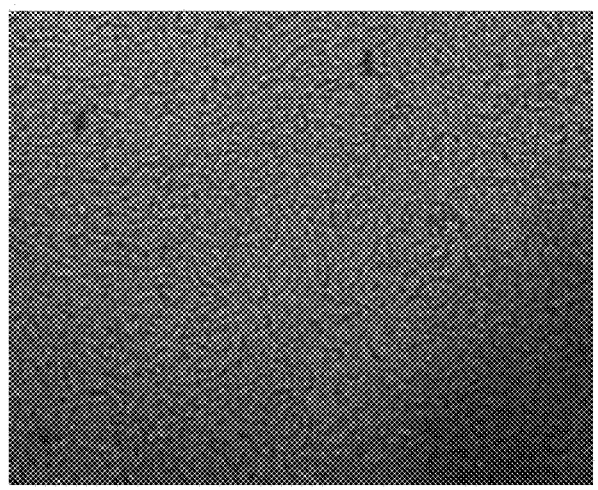

FIG. 5A depicts the morphology and density of pericytes upon initial plating of the cells upon the astrocyte cell layer that had proliferated for 48 hours. FIG. 5B depicts the morphology of the pericytes after the cells have proliferated for 48 hours on top of the astrocytes.

Figure 6A:
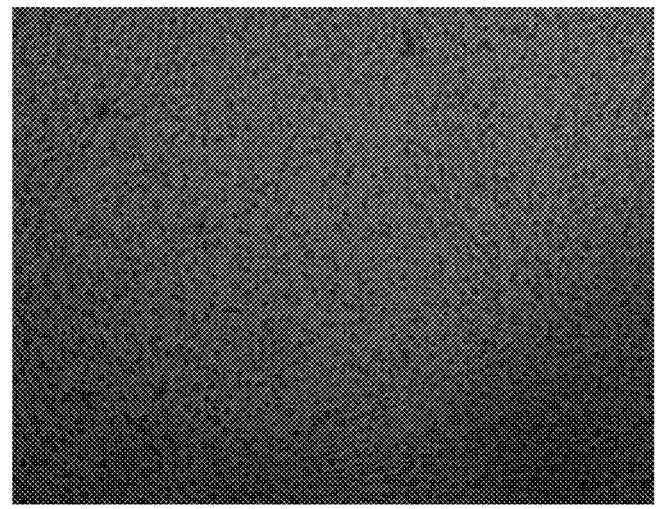
FIGS. 6A~6B show the culturing a layer of hCMEC/D3 cells after step II.
Figure 6B:
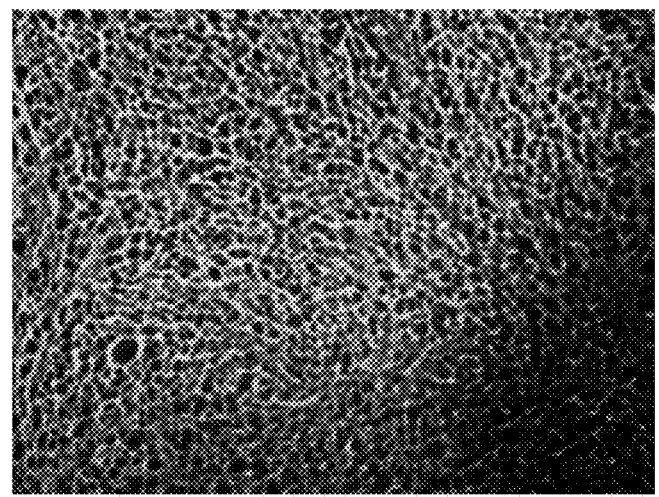

FIG. 6A depicts the morphology and density of hCMEC/D3 cells upon initial plating of the cells on top of the astrocyte-pericyte coculture. FIG. 6B depicts the morphology of the hCMEC/D3 after the cells have proliferated for 48 hours on top of the other cell layers.

Figure 7A:
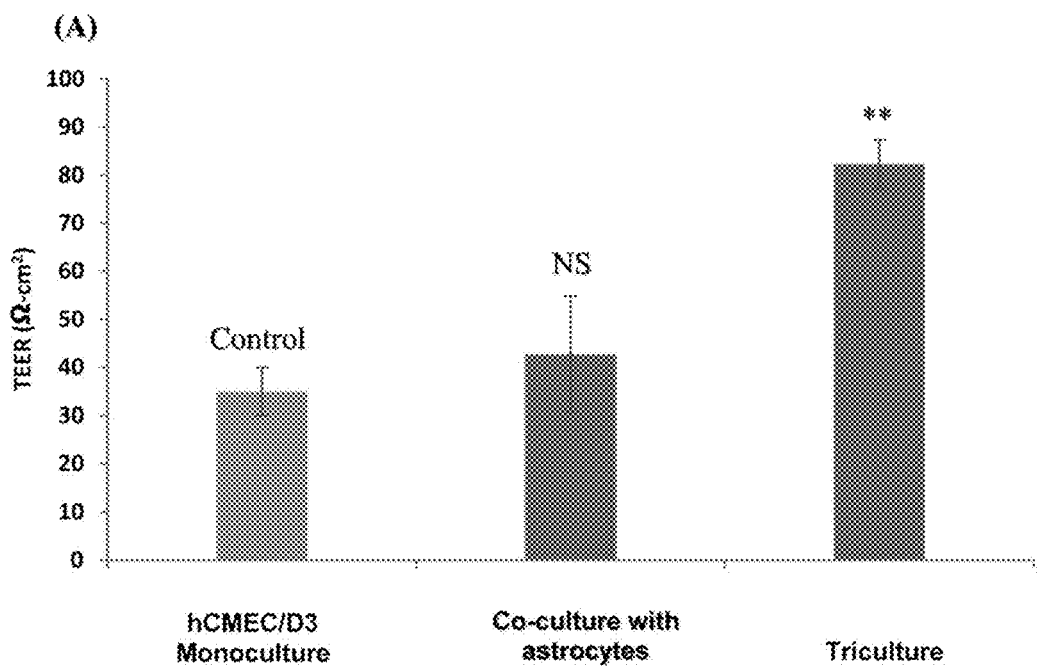
FIGS. 7A~7B show a comparison of paracellular tightness in the mono-, co- and tri-culture models of the BBB. TEER values.
Figure 7B:
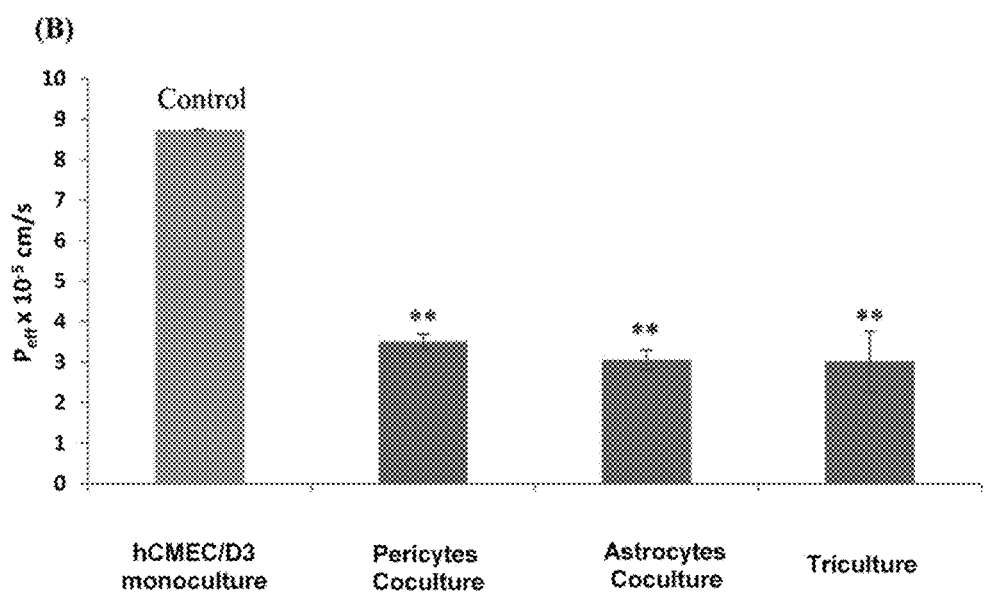

FIG. 7A shows a chart of the representative TEER values of the hMCEC/D3 monoculture, direct contact coculture, and direct contact triculture in comparison to one another. The TEER values for the coculture and triculture are higher than that of the monoculture alone, with the triculture being significantly higher than the other two models. This suggest that the incorporation of additional cell lines in direct contact aids in the formation of restrictive tight junctions. FIG. 7B shows a chart of permeability of sucrose across the cell models, also suggesting that the triculture forms significantly more restrictive tight junctions in comparison to the other models as shown by the significantly decreased permeability coefficient.

Figure 8A:
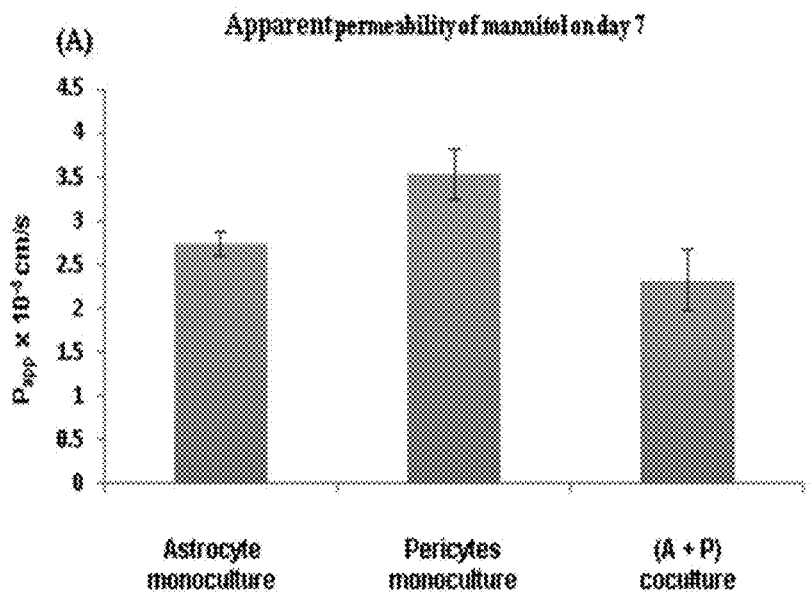
FIGS. 8A~8B show the permeability of mannitol across mono- or co-cultures of astrocytes and pericytes.
Figure 8B:
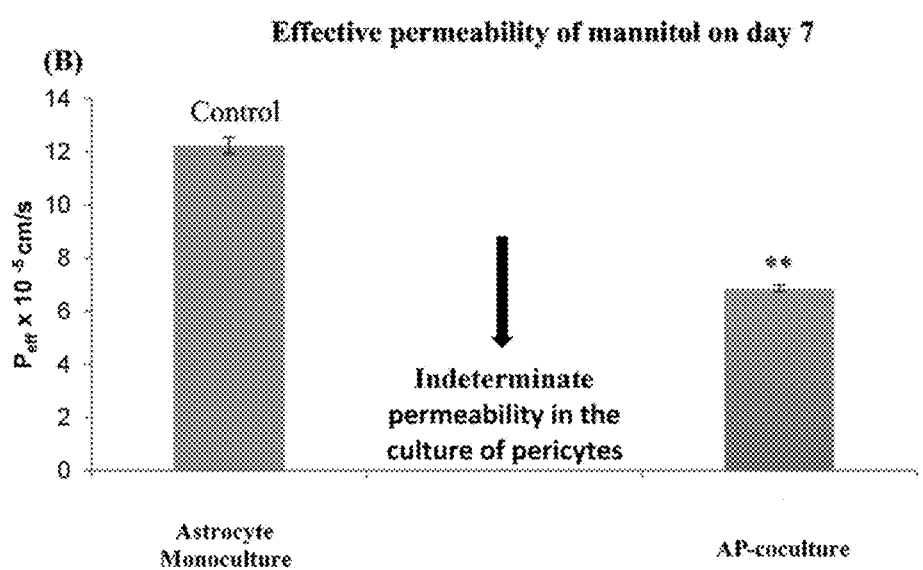

FIG. 8A shows a chart of the interaction of the pericytes and astrocytes. Astrocytes monoculture poses more resistance to the paracellular transport of mannitol in comparison to the pericytes monoculture. Indeed, resistance to mannitol permeability across the pericytes monoculture is similar to that across free filter supports. Therefore, pericytes may not be contributing to the resistance for mannitol permeability. Interestingly, a coculture of astrocytes and pericytes seem to lower the average value of mannitol permeability. FIG. 8B shows a chart of the effect of pericytes on the effective permeability of mannitol across the astrocytes layer. The effective permeability of mannitol is significantly reduced in the astrocytes-pericytes coculture.

Figure 9:
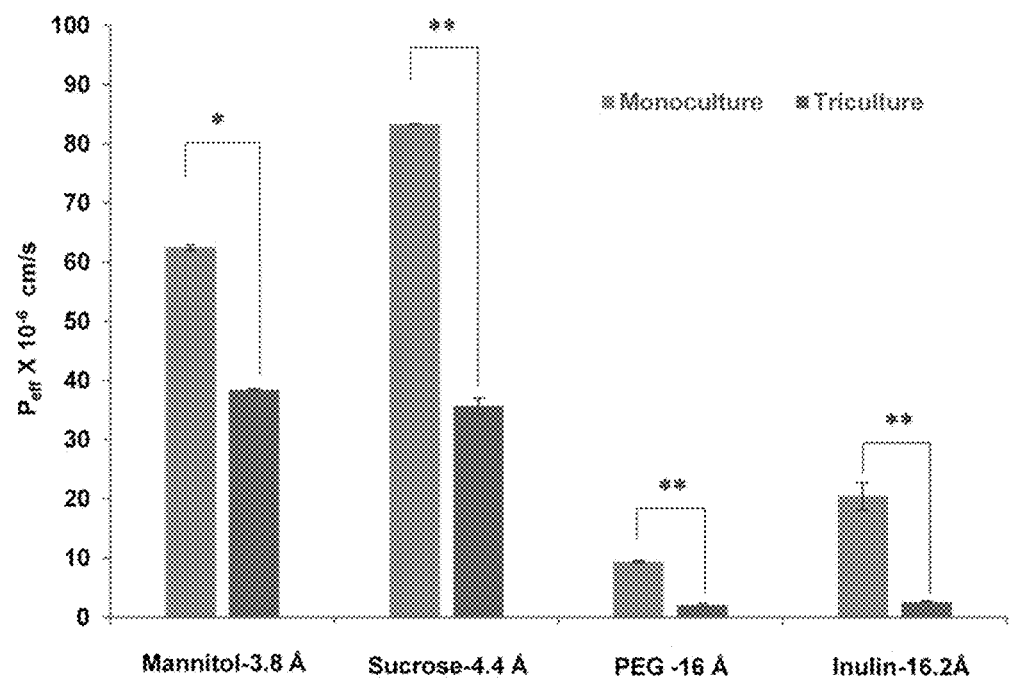
FIG. 9 shows a size-dependent reduction of paracellular permeability. In comparing mono- and tri-cultures, the decrease in permeability was 1.5-fold for mannitol, 2.4-fold for sucrose, 4.5-fold for PEG-4000, and 8-fold for Inulin-5000. The larger compounds would be much more restricted in the triculture than in the monoculture models of the BBB system. One-tailed student t-test was used to determine statistically significant difference, where hCMEC/D3 monocultures acted as controls, n=5, *$P<0.05$, **$P<0.01$.

FIG. 9 shows the reduction in paracellular permeability in the monoculture as compared to the triculture. The triculture results in a significant reduction in paracellular permeability for all markers compared to the monoculture. This suggests that the triculture is better at restricting permeation than the monoculture. The models show that permeability decreases with increasing size of the markers.

Figure 10A:
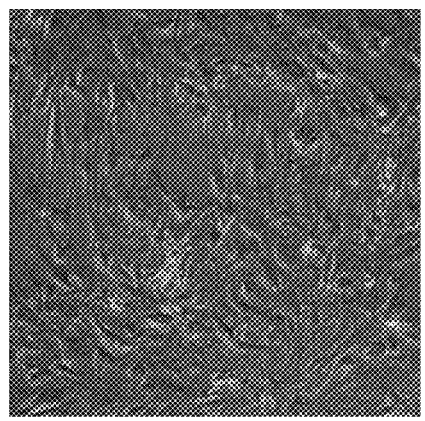
FIGS. 10A~10C show the formation of distinct cell-layers during BBB triculture preparation.
Figure 10B:
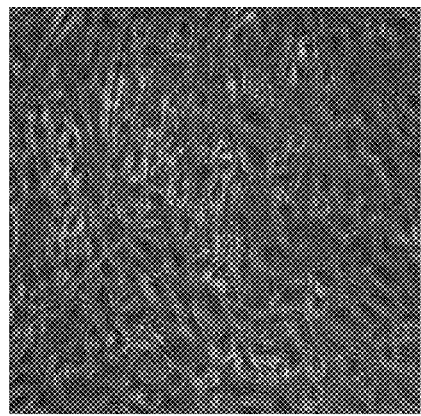
Figure 10C:
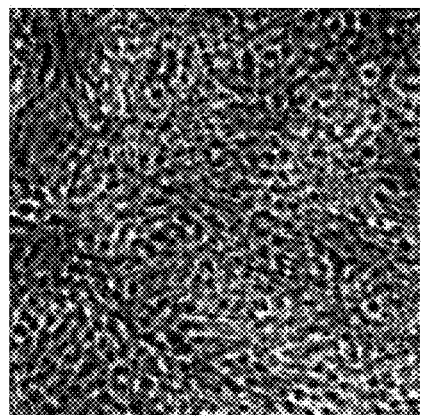

FIG. 10 shows the formation of distinct layers of cells during culture preparation of the triculture. The morphology and confluency of each layer is distinct from one another as cell layers are plated and allowed to proliferate.

Figure 11A:
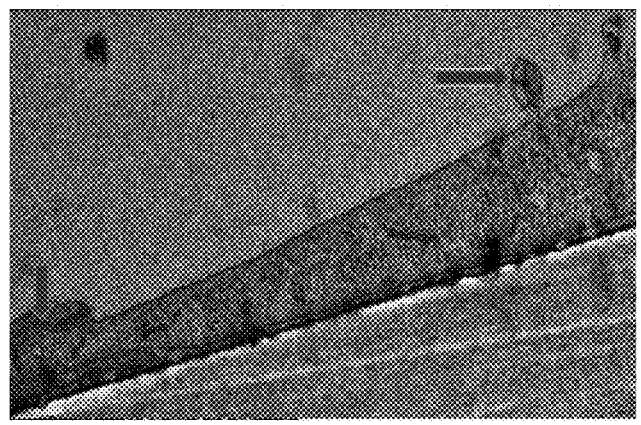
FIGS. 11A~11C show the ultrastructural features in the hCMEC/D3 cells.
Figure 11B:
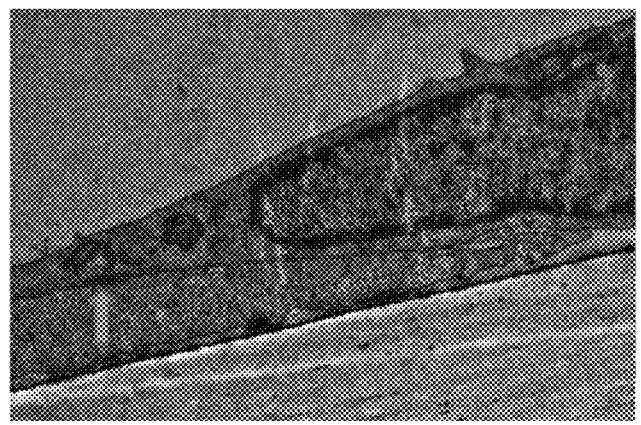
Figure 11C:
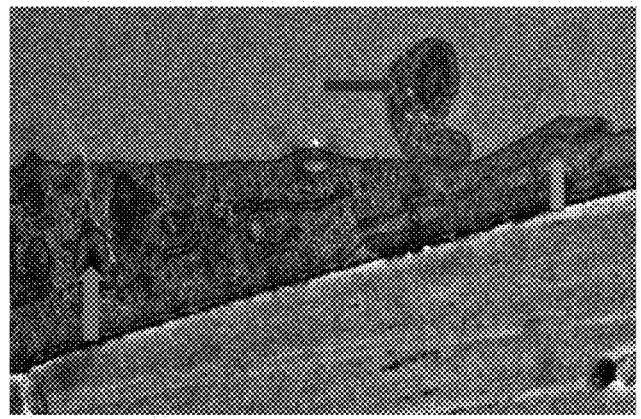

FIGS. 11A, 11B, and 11C show the ultrastructural features of the hCMEC/D3 as it forms tight junctions and undergoes proliferation.

Figure 12A:
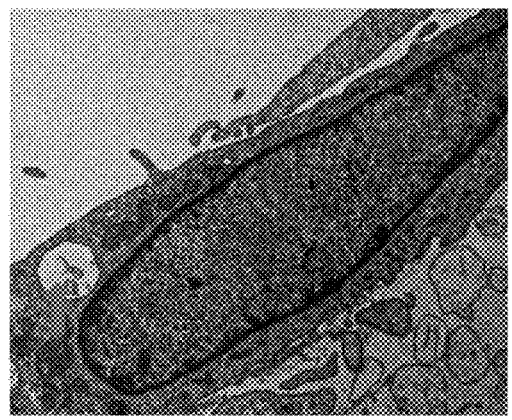
FIGS. 12A~12C show the ultrastructural features in pericytes.
Figure 12B:
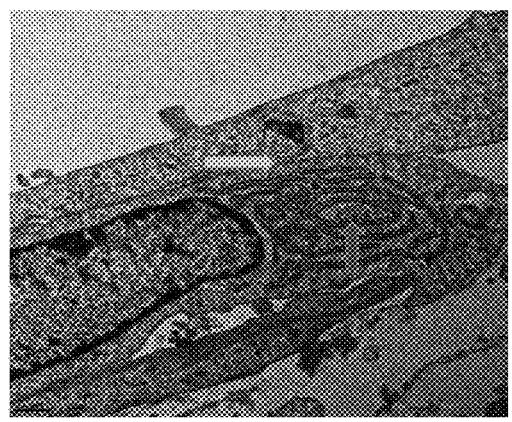
Figure 12C:
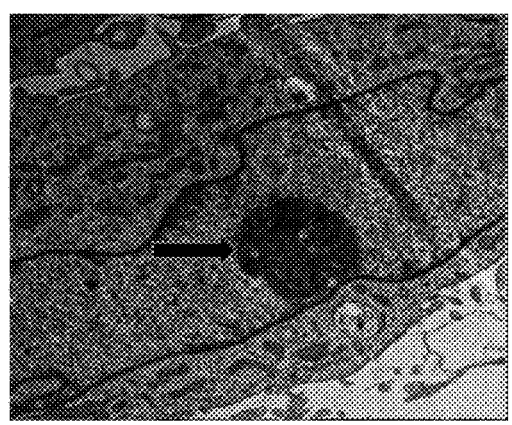

FIGS. 12A, 12B and 12C show the ultrastructural features of the pericytes as they form wide cell-cell junctions, exhibit prominent rough endoplasmic reticulum, and a dark nucleus.

Figure 13A:
FIGS. 13A~13C show the ultrastructural features in astrocytes. Panel.
Figure 13B:
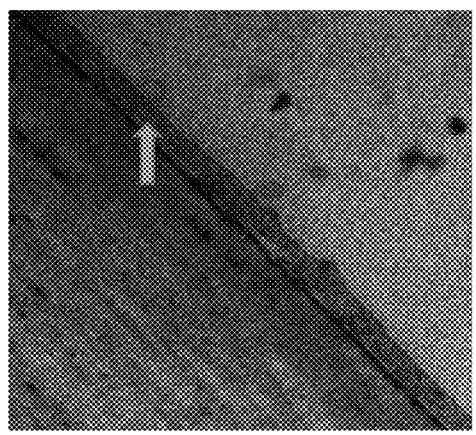
Figure 13C:
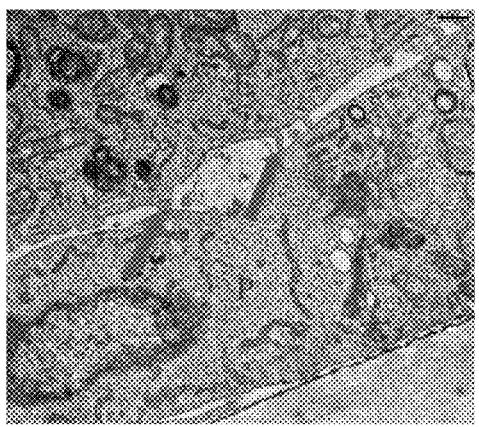

FIGS. 13A, 13B and 13C show the ultrastructural features of the astrocytes as they form satellite and elongated projections from the cell body.

Figure 14A:
FIGS. 14A~14C depict the ultrastructural features in the layers of a co-culture of hCMEC/D3 cells atop the pericytes lawn.
Figure 14B:
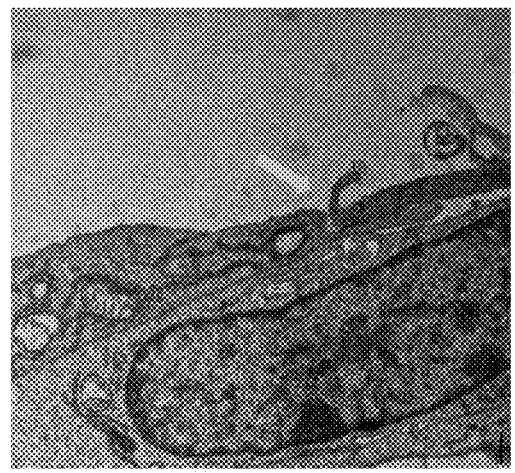
Figure 14C:
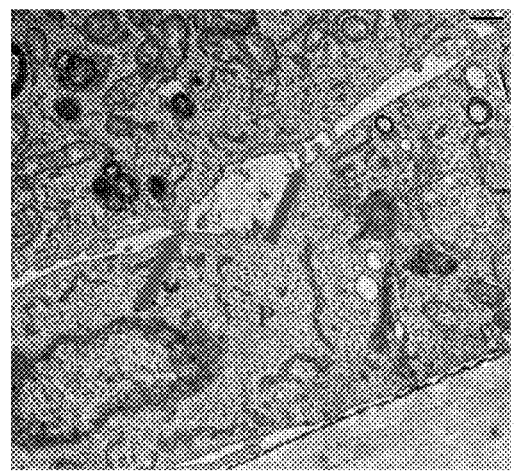

FIGS. 14A, 14B, and 14C depict the ultrastructural features in the layers of a co-culture of hCMEC/D3 cells atop the pericytes lawn showing two cells with similar morphologies apposed in a layered configuration. Additionally cells are shown to be forming tight cell junctions and cell-cell connections formed through gap spaces between two adjacent cells. Direct cell-cell contacts/gap junctions may be relevant in conveying signaling molecules between BBB cells or as novel routes for drug delivery across the BBB cell layers into the brain parenchyma.

Figure 15A:
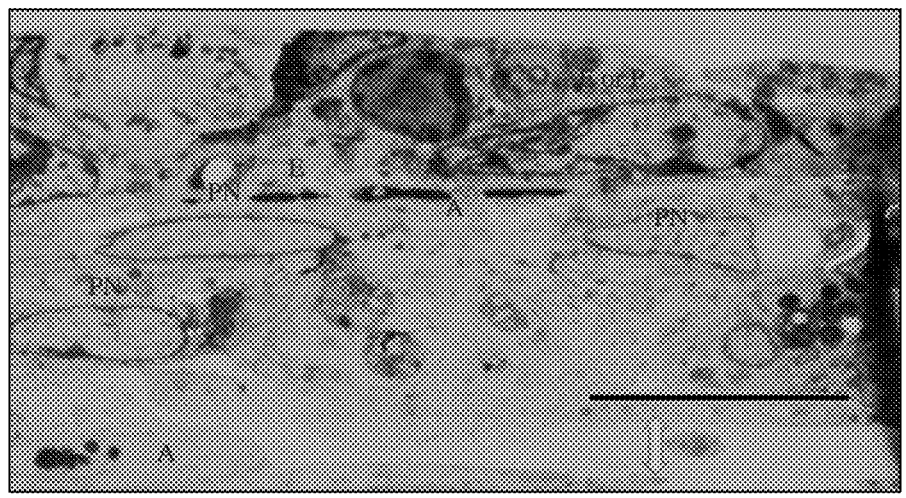
FIGS. 15A~15B depict the cross-sectional arrangement of cells in the triculture model, part I.
Figure 15B:
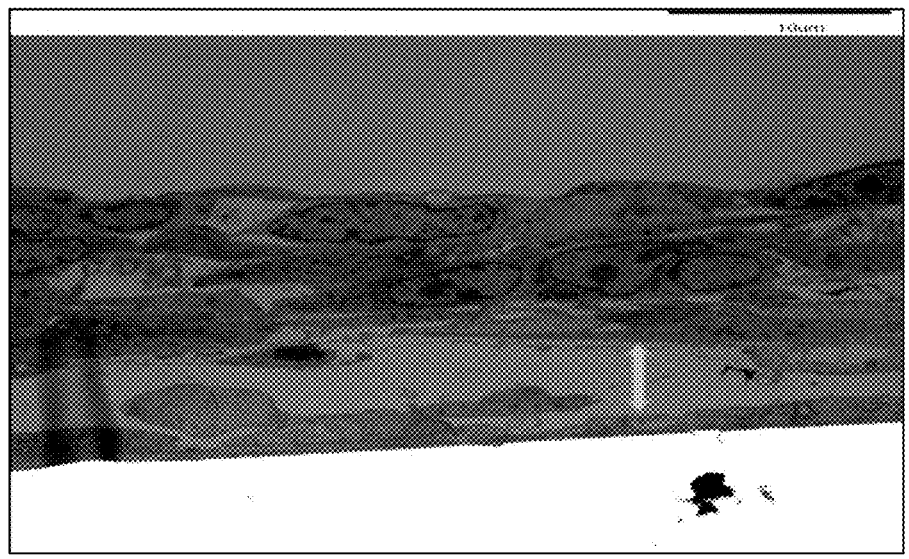

FIGS. 15A and 15B show a cross-sectional arrangement of cells in the triculture model showing the cells plated in direct contact in three separate layers. The cells have been identified based on the independent cell morphologies seen in FIGS. 11~13.

Figure 16A:
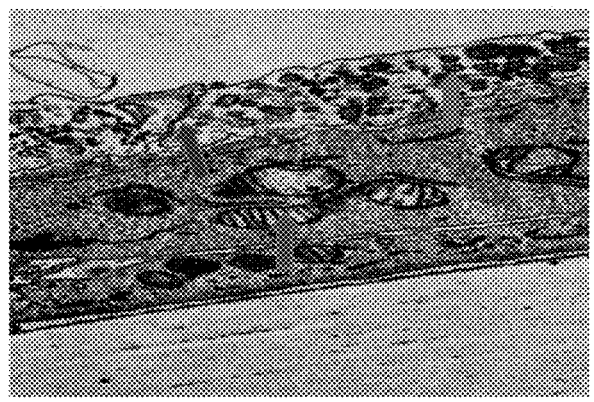
FIGS. 16A~16C depict the cross-sectional arrangement of the BBB-cells in the triculture model, part II.
Figure 16B:
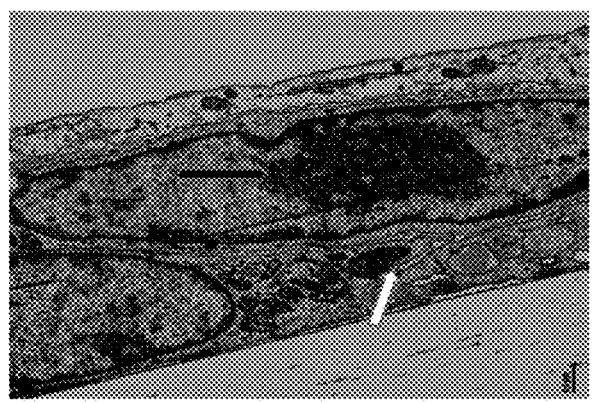
Figure 16C:
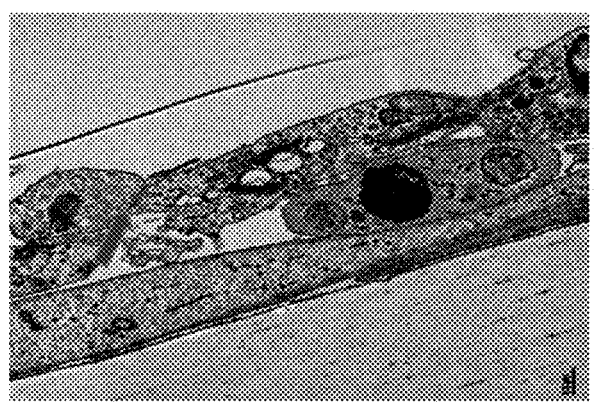

FIGS. 16A, 16B, and 16C show a cross-sectional image of the triculture model where cells are identified in distinct layers in direct contact based on the individual morphology and identifying factors.

Figure 17:
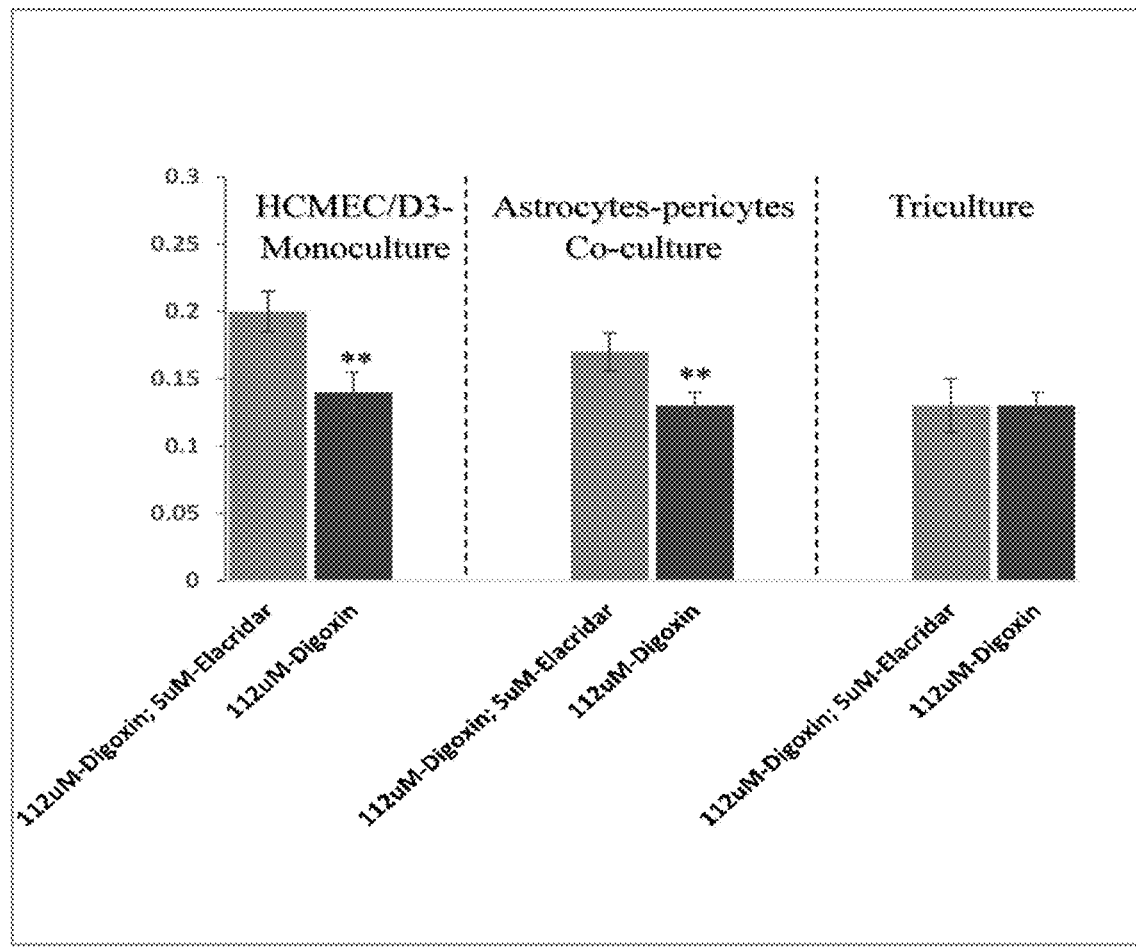
FIG. 17 shows a comparison of drug-interactions (Elacridar and digoxin) in the AP-coculture versus hCMEC/D3 monoculture, and the triculture. Under similar inhibitory concentration, it is seems to be more difficult to inhibit Pgp function in the triculture in comparison to the hCMEC/D3 monoculture or the co-culture of astrocytes and pericytes (a comparison of efflux inhibition using separate BBB-cellular constituents or the BBB-cellular constituents in a direct assembly). Statistical significant difference was tested using one-tailed Student's t-test, n=6 in each case, and **P<0.01 was considered statistically significant difference.

FIG. 17 shows a comparison of drug-interactions of elacridar and digoxin in the monoculture, astrocyte-pericyte coculture, and triculture models. Under similar inhibitory concentration, it is seems to be more difficult to inhibit Pgp function in the triculture in comparison to the hCMEC/D3 monoculture or the co-culture of astrocytes and pericytes.

Figure 18:
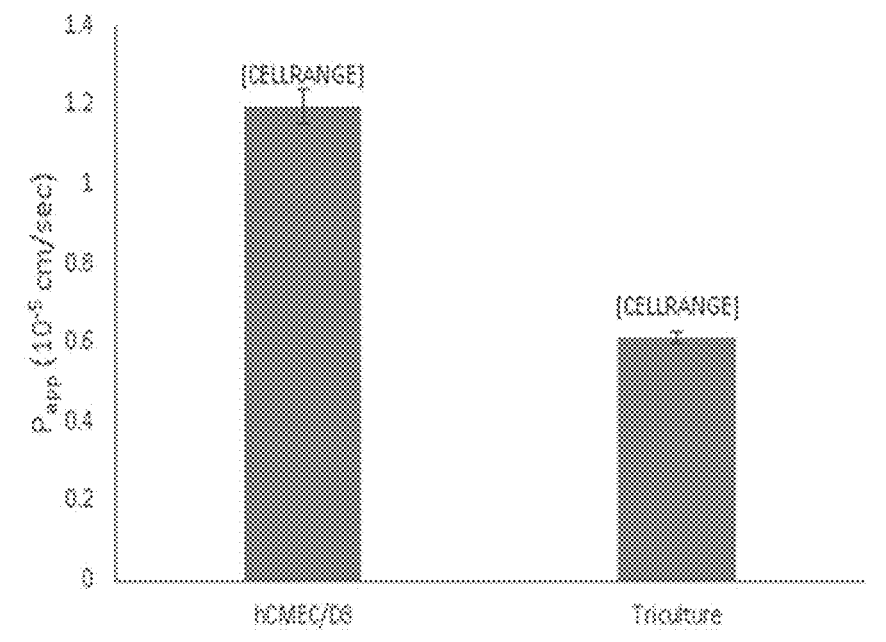
FIG. 18 shows the apparent permeability of transcellular marker, fluoxetine (a Pgp-substrate) at a concentration of 20 µg/mL across the hCMEC/D3 monoculture and direct contact triculture models. Studies were run in triplicate and subjected to Student's t-test. Significant changes are noted with (**) for P<0.01. Error bars represent 1 standard deviation (n=3)

FIG. 18 depicts the permeability of the transcellular marker, fluoxetine, across the hCMEC/D3 monoculture and triculture models. The decrease in permeability in the triculture suggest that the direct contact of the cells also enables restriction across other routes of permeation.

Figure 19:
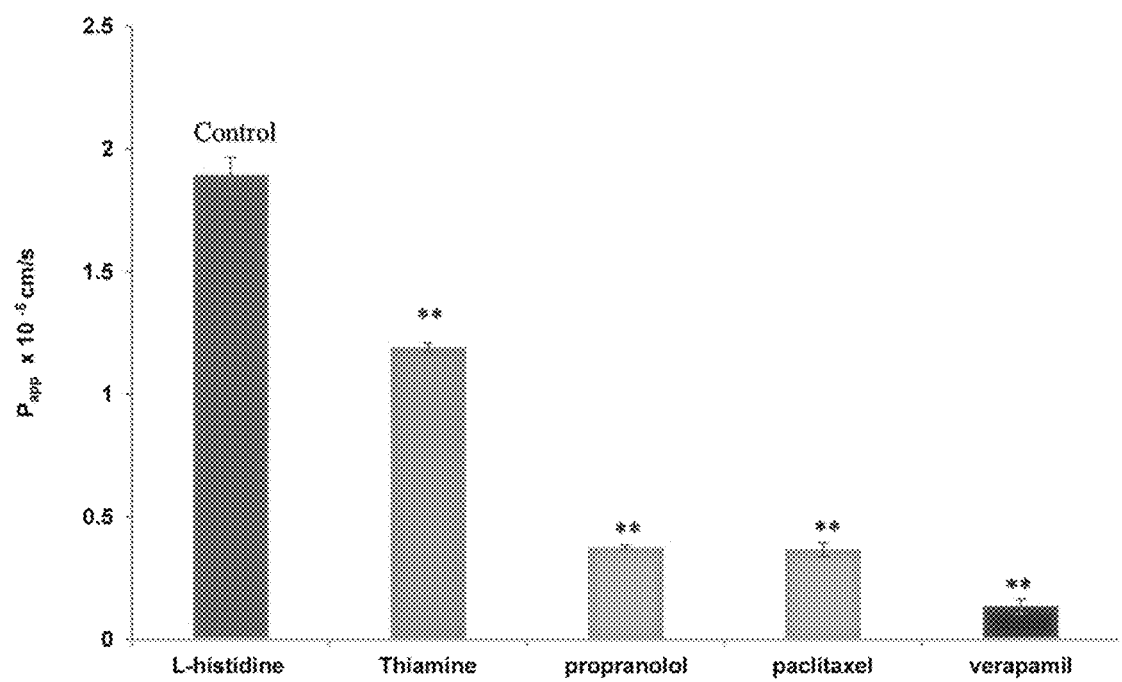
FIG. 19 shows the selective transcellular permeability across the BBB-triculture on a Transwell® membrane. Green compounds fast permeability, yellow compounds show intermediate permeability and red compound show low permeability. Note that Thiamine, propranolol, paclitaxel, and verapamil (all Pgp substrates) were significantly slower than L-histidine (a non-Pgp substrate positive control). One-tailed Student's t-test was used to determine statistically significant difference, n=3 in each case; *P<0.05, and **P<0.01.

FIG. 19 represents the selective transcellular permeability across the triculture model. The extent a molecule crosses the triculture is dependent on its route of permeation.

Figure 20:
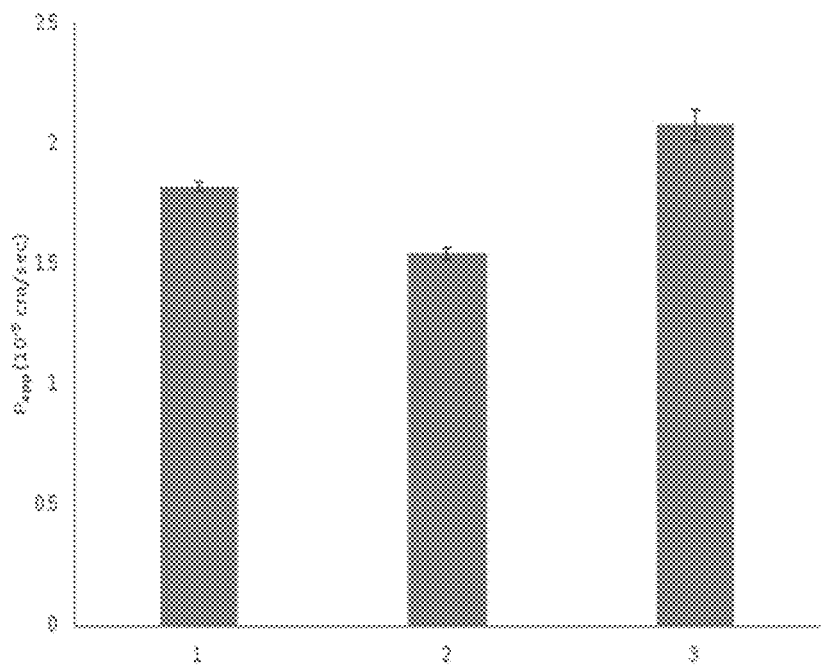
FIG. 20 shows the apparent permeability of [$^{14}$C]-mannitol across the iCell® Endothelial cell triculture in direct contact under different medium conditions. Medium was supplemented as recommended by Cellular Dynamics International Inc (1), EBM-2 as it is supplemented for hCMEC/D3 (2), and DMEM supplemented with 1% FBS and 20 ng/mL bFGF (3). Studies were performed to determine the optimal medium composition for culture of the iPSC derived BMECs when in the direct contact triculture. Permeability was conducted in triplicate. Error bars represent 1 standard deviation (n=3)

FIG. 20 depicts the permeability of mannitol across a triculture using stem cell derived BMECs to determine the optimal medium composition for these BMECs when used in the direct contact triculture.

Figure 21:
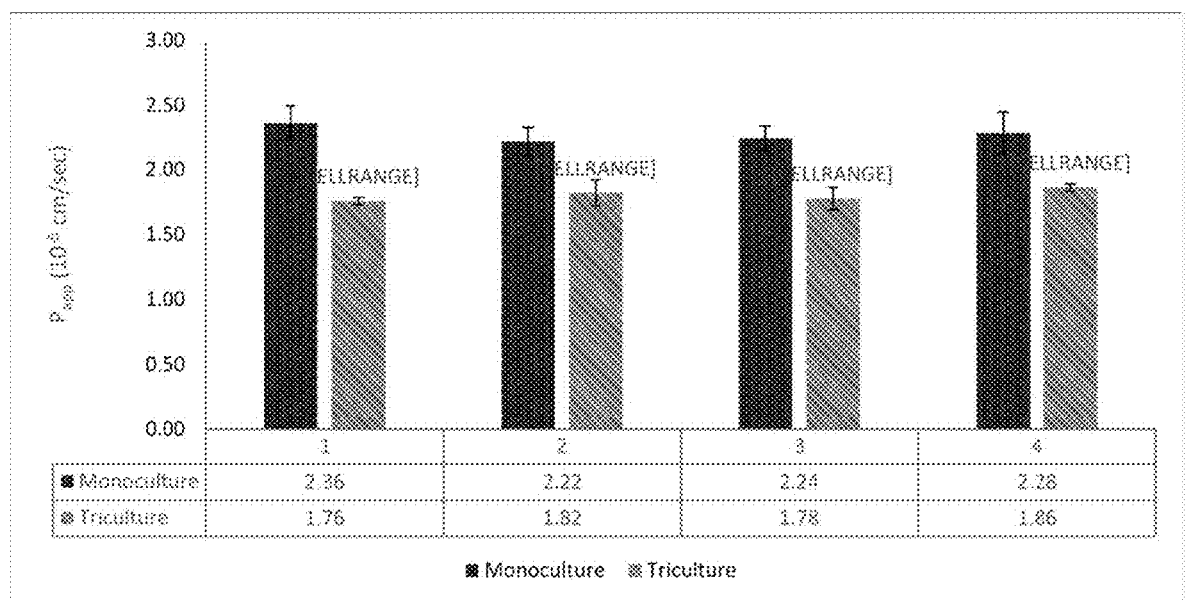
FIG. 21 shows the apparent permeability of [$^{14}$C]-mannitol to assess the impact of retinoic acid as a medium supplement for the iCell® Endothelial cell monoculture and triculture. Retinoic acid is an established molecule that induces cell differentiation, and was not added to EBM-2 supplemented media that was used for other studies with hCMEC/D3 cells. (1), added only upon plating of iPSC-BMECs and maintained throughout culture (2), added to the culture flask 48 hours prior to plating and not maintained throughout culture (3), or added to the culture flask 48 hours prior to plating and maintained throughout culture (4). Retinoic acid was added only to the apical chamber at 10 µM. All studies were performed in triplicate and subjected to Student's t-test. Significant changes are noted with (*) P<0.05 or (**) P<0.01. Error bars represent 1 standard deviation (n=3)

FIG. 21 shows a chart of mannitol permeability and how it is impacted by the addition of retinoic acid as a medium supplement and different time during culturing of the stem cell derived BMEC triculture.

FIG. 22A represents a schematic of prior models of the BBB using multiple cell lines where the astrocytes are plated on the basolateral side of the filter support with BMECs on the apical side. FIG. 22B represents a schematic of the direct contact coculture that is used in studies that are disclosed herein, where both cell types are plated on the same side of a cell culture surface, in direct contact.

Figure 23A:
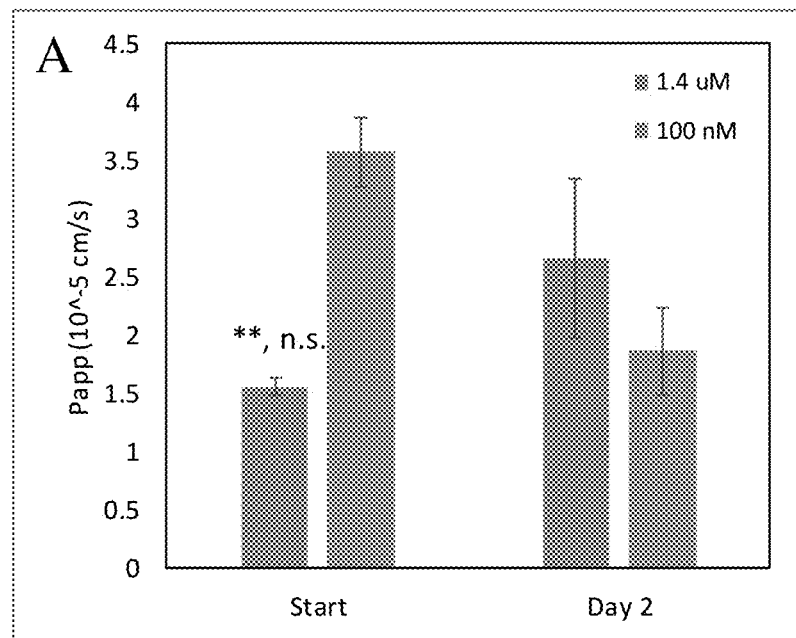
FIGS. 23A~23C show the Optimization of direct contact culture using apparent permeability of [14C]-Mannitol.
Figure 23B:
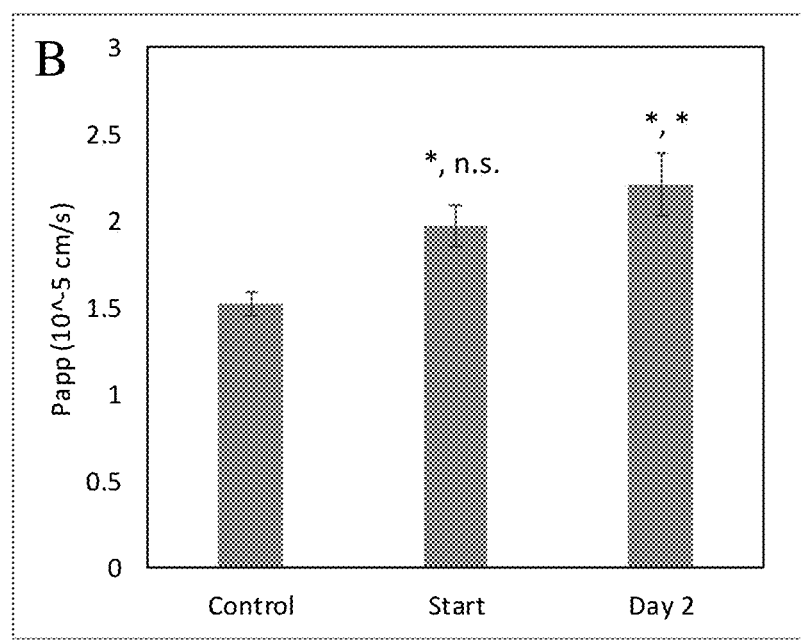
Figure 23C:
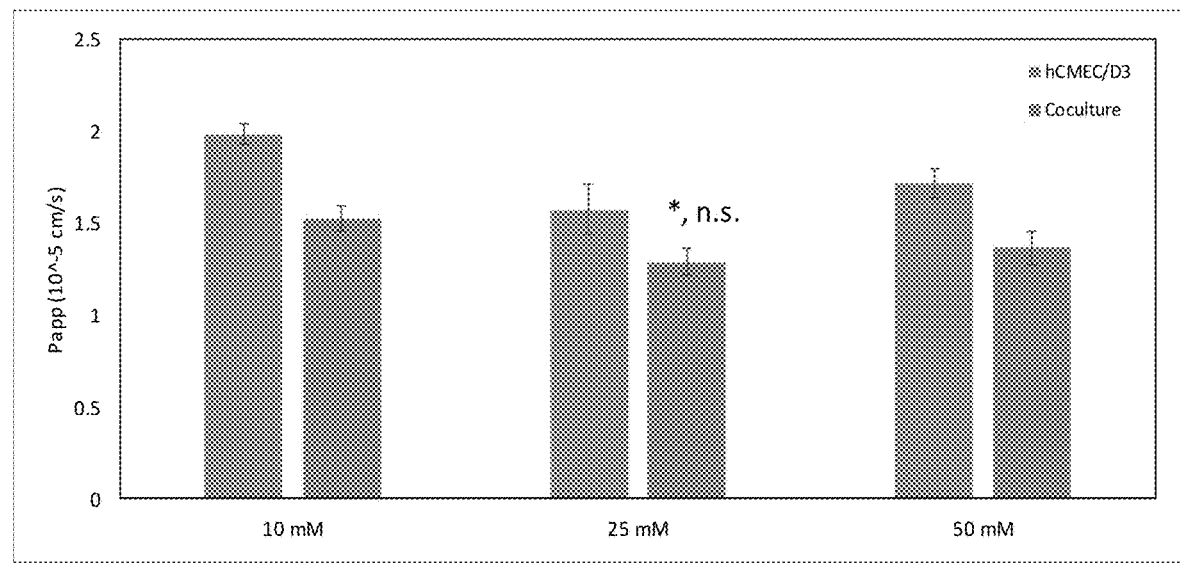

FIGS. 23A, 23B and 23C describe optimization of direct contact culture using apparent permeability of [$^{14}$C]-mannitol. FIG. 23A shows hydrocortisone added to media at 1.41 M or 100 nM at the start of human cerebral microvessel endothelial cells plating or 2 days postplating. FIG. 23B shows lithium chloride at 10 mM compared with control (0 mM) when added at the start of human cerebral microvessel endothelial cells plating or 2 days postplating. FIG. 23C shows 4-(2-hydroxyethyl)-1-piperazineethanesulfonic acid concentrations of 10, 25 and 50 mM added to media for human cerebral microvessel endothelial cells monolayer in comparison with direct culture. Studies were run in triplicate and subjected to Student's t-test and Mann-Whitney test (FIGS. 23A and 23C) or one-way ANOVA with Bonferroni post-hoc test or Kruskal-Wallis with Dunn's post-hoc test (FIG. 23B). Significant changes are noted with an asterisk (*) for P<0.05 and (**) for P<0.01. Significant levels are reported as (t-test, MW) or (one-way ANOVA, KW). Error bars represent 1 standard deviation (n=3).

Figure 24:
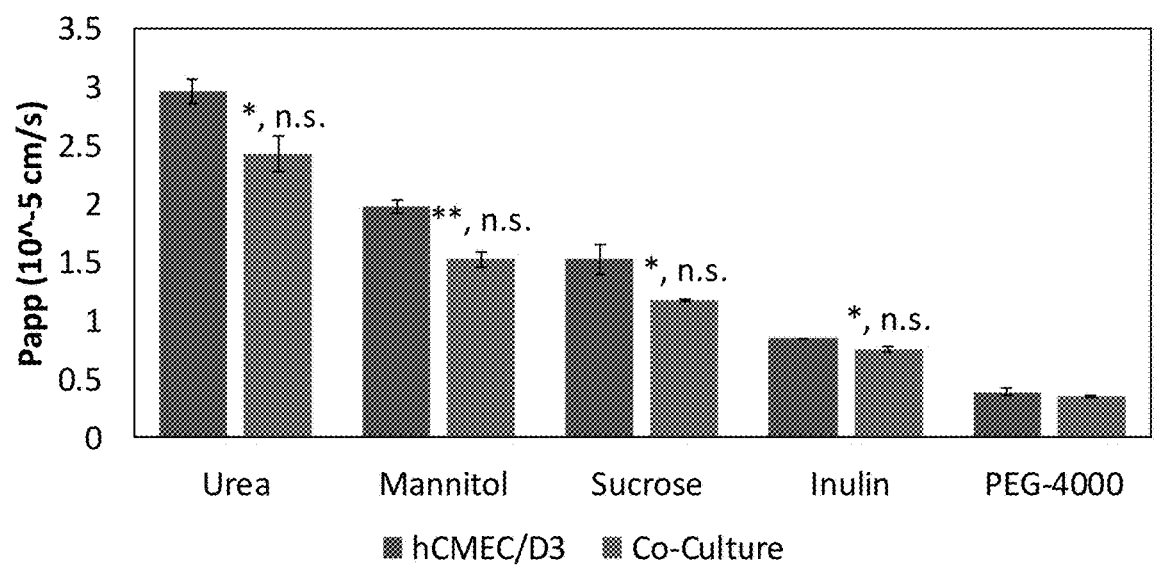
FIG. 24 shows a chart of the apparent permeability for 5 paracellular [$^{14}$]-labeled markers of various hydrodynamic radii. Studies were run in triplicate and subjected to student's T-Test or Mann-Whitney test. Significant changes are noted with an asterisk (*) for p<0.05 and (**) for p<0.01. Significant levels are reported as (t-test, MW). Error bars represent 1 standard deviation (n=3)

FIG. 24 depicts apparent permeability for five paracellular [$^{14}$C]-labelled markers of various hydrodynamic radii. Studies were run in triplicate and subjected to Student's t-test or Mann-Whitney test. Significant changes are noted with an asterisk (*) for P<0.05 and (**) for P<0.01. Significant levels are reported as (t-test, MW). Error bars represent 1 standard deviation (n=3).

FIG. 25 shows the apparent permeability of [$^{14}$C]-inulin, a paracellular marker, across the direct contact coculture. Studies were subjected to one-way ANOVA with a Bonferroni post-hoc test and Kruskal-Wallis with Dunn's post-hoc test. Significant changes are noted with an asterisk (*) for P<0.05 and (**) for P<0.01. Significant levels are reported as (one-way ANOVA, KW). Error bars represent 1 standard deviation (n=6).

FIG. 26 describes the apparent permeability of [$^{14}$C]-mannitol and [$^{14}$C]-sucrose across direct and indirect contact cocultures. Studies were run in triplicate and subjected to Student's t-test or Mann-Whitney test. Significant changes are noted with an asterisk (*) for P<0.05 and (**) for P<0.01. Significant levels are reported as (t-test, MW). Error bars represent 1 standard deviation (n=3).

FIG. 27 describes the apparent permeability of [$^{14}$C]-propranolol, a passive transcellular permeability marker. Studies were subjected to one-way ANOVA with a Bonferroni post-hoc test and Kruskal-Wallis with Dunn's post-hoc test. Non-significant changes (P>0.05) were seen between monoculture and coculture. Error bars represent 1 standard deviation (n=3)

Figure 28:
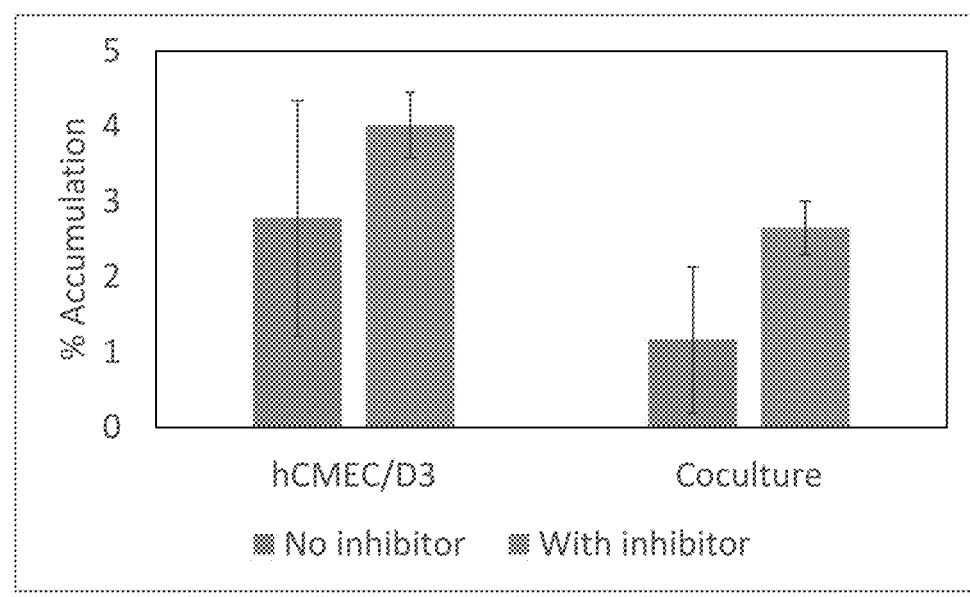
FIG. 28 shows the total percentage of accumulation of rhodamine 123 to show functional expression of efflux transporter P-glycoprotein in hCMEC/D3 monoculture and direct contact coculture. Efflux of P-gp substrate rhodamine 123 was assessed in the presence and absence of P-gp inhibitor verapamil. Studies were subjected to one-way ANOVA with a Bonferroni post hoc test and Kruskal-Wallis with Dunn's post-hoc test. No significant difference was observed between the presence and absence of inhibitor for either model (p>0.05). Error bars represent 1 standard deviation (n=3).

FIG. 28 shows the total percentage of accumulation of rhodamine 123 to show functional expression of efflux transporter P-glycoprotein in human cerebral microvessel endothelial cells monoculture and direct contact coculture. Efflux of P-gp substrate rhodamine 123 was assessed in the presence and absence of P-gp inhibitor verapamil. Studies were subjected to one-way ANOVA with a Bonferroni post hoc test and Kruskal-Wallis with Dunn's post-hoc test. No significant difference was observed between the presence and absence of inhibitor for either model (P>0.05). Error bars represent 1 standard deviation (n=3).

Cell Culture Optimization

In order to delineate changes in BBB phenotype upon hCMEC/D3 coculture with human astrocytes, permeability was measured with a number of marker compounds. The hCMEC/D3 monoculture cells and the indirect coculture models were used for comparison. However, the direct coculture model was first optimized for minimal paracellular permeability.

Hydrocortisone was utilized as a media additive due to its endogenous role as an anti-inflammatory agent that increases tight junctional integrity. Permeability studies were conducted using 1.4 µM and 100 nM at the start of hCMEC/D3 culture or after two days of proliferation. Results in FIG. 23A showed that 1.4 µM hydrocortisone at the start of hCMEC/D3 plating provided the lowest [$^{14}$C]-Manntiol permeability compared 100 nM ($1.54\pm0.07\times10^{-5}$ cm/s and $3.56\pm0.29\times10^{-5}$ cm/s; t-test, p=0.005; Mann-Whitney, p=0.100).

Lithium chloride was selected as a media additive because of its implications in the Wnt/β-catenin pathway and increase in tight junctional protein expression (Paolinelli, R. M., et al., *PLos One*, 2013, 8 (8): 11). Lithium chloride, at a concentration of 10 mM, was added to media at the start of hCMEC/D3 plating or two days after. Results in FIG. 23B showed that lithium chloride addition at the start of plating and at Day 2 both increased [$^{14}$C]-Mannitol permeability compared to no LiCl addition ($2.20\pm0.18\times10^{-5}$ cm/s, $1.97\pm0.12\times10^{-5}$ cm/s and $1.52\pm0.07\times10^{-5}$ cm/s; one-way ANOVA Bonferroni, p=0.036 and p=0.028; Kruskal-Wallis Dunn's test, p=0.408 and p=0.034).

The hCMEC/D3 cell line has been shown to be sensitive to small changes in pH; therefore, HEPES concentration was optimized to limit pH changes during cell culturing (Zougbede, S. et al, *J. Cerebral Blood Flow Metabolism* 2011, 31 (2): 514-526). HEPES was studied at 10 mM, 25 mM, and 50 mM on both the direct cocutlure an hCMEC/D3 monolayers. The direct coculture was found to be less permeable than hCMCEC/D3 monolayers at all HEPES concentrations with 25 mM showing the best results for decreased permeability of [$^{14}$C]-Mannitol and minimal toxicity for the direct coculture ($1.28\pm0.07\times10^{-5}$ cm/s; t-test, p=0.033; Mann-Whitney, p=0.100) as seen in FIG. 23C. MTT assay results showed an insignificant reduction in cell viability (−8.2±2.0%; p>0.05) for 25 mM HEPES sample in comparison to 10 mM HEPES. A HEPES concentration of 50 mM resulted in a significant decrease in cell viability (−28.4±2.6%; one-way ANOVA Bonferroni, p=0.00003; Kruskal-Wallis Dunn's test, p=0.001) when compared to a 10 mM HEPES control.

TABLE 3

Optimization of the Direct Contact Coculture Model.

| Attribute | Range | Optimized Value |
|---|---|---|
| hCMEC/D3 Seeding Density | 50,000-250,000 cells/cm² | 100,000 cells/cm² |
| Astrocyte Seeding Density | 10,000-40,000 cells/cm² | 40,000 cells/cm² |
| Basement Matrix | Collagen, Poly-L-Lysine, MaxGel, Fibronectin | Poly-L-Lysine |
| Seeding Time | 3, 5, 7, 9, 11, 13, 15, 17, 19 Days | 7 Days |
| Seeding Order | Separate vs Concurrent Plating | Separate |
| Media | EBM-2 vs Astrocyte Medium | EBM-2 |
| Fetal Bovine Serum | Serum vs. Serum-Free | Serum |
| Hydrocortisone | 100 nM-1.4 µM | 1.4 µM |
| HEPES | 10 mM-50 mM | 25 mM |
| Lithium Chloride | 0 mM-10 mM | 0 mM |

TABLE 4

Comparison of molecular weight and molecular radii with apparent permeability of paracellular model compounds.*

| Marker | Molecular Weight | Stokes Radius (Å) | Hydrodynamic Radius (Å) | $P_{app}$ ($\times 10^{-5}$ cm/s) |
|---|---|---|---|---|
| Urea | 60 | 1.7 | 1.8 | 2.43 ± 0.155 |
| Mannitol | 182 | 3.6 | 4.3 | 1.52 ± 0.069 |
| Sucrose | 342 | 4.6 | 5.2 | 1.17 ± 0.008 |
| Inulin | 5000 | 13.9 | 10 | 0.754 ± 0.030 |
| PEG-4000 | 4000 | 16.4 | 15.9 | 0.357 ± 0.010 |

*Ghandehari H, et al., *J Pharmacol Exp Ther* 1997, 280(2): 747-753; Schultz S G, et al., *J Gen Physiol* 1961, 44: 1189-1199.

An extensive design of experiments (DOE) was used for optimization of hCMEC/D3 and astrocyte seeding density, basement matrix, media additives, and seeding time prior to the following studies. These attributes were assessed using TEER and paracellular permeability markers with all studies performed in triplicate. Results of the optimization are shown in Table 3.

Paracellular Permeability—Direct Contact Coculture

As noted above, the hCMEC/D3 cell line, while tighter than other immortalized human BMEC cells, possess tight junctions that lack ideal physiological relevance. To investigate changes in tight junction pore radius, five marker compounds of varying hydrodynamic radii were used to determine changes in paracellular permeability. As expected, increases in hydrodynamic radii lead to decreased apparent permeability coefficients for paracellular markers. However, the extent of changes in permeability varied between mono- and coculture, likely due to the effects predicted by the Renkin molecular sieving function as the pore radii approaches the size of the sieved molecule (Carl, S. M., et al., *Mol Pharm*, 2010, 7 (4): 1057-1068). Although it should be noted that in the presence of astrocytes, the assumptions made by the Renkin function including the presence of a single pore, varied and increased tortuosity and porosity exists. Thus, the effects of permeation across the astrocytes cannot be easily corrected to obtain a pore radius.

As shown in FIG. 24, decreases in paracellular permeability from the mono- and coculture were seen for [$^{14}$C]-urea (2.96±0.11×10$^{-5}$ cm/s and 2.43±0.15×10$^{-5}$ cm/s; t-test, p=0.030; Mann-Whitney, p=0.100), [$^{14}$C]-mannitol (1.98±0.05×10$^{-5}$ cm/s and 1.52±0.07×10$^{-5}$ cm/s; t-test, p=0.001; Mann-Whitney, p=0.100), [$^{14}$C]-sucrose (1.52±0.13×10$^{-5}$ cm/s and 1.17±0.008×10$^{-5}$ cm/s; t-test, p=0.044; Mann-Whitney, p=0.100), and [$^{14}$C]-inulin (8.46±0.02×10$^{-6}$ cm/s and 7.55±0.3×10$^{-6}$ cm/s; t-test, p=0.034; Mann-Whitney, p=0.100) respectively. The smallest decrease was seen for [$^{14}$C]-PEG-4000 (3.93±0.36×10$^{-6}$ and 3.57±0.10×10$^{-6}$ cm/s; t-test, p=0.227; Mann-Whitney, p=0.100).

The direct contact coculture was assessed for reproducibility by repeating paracellular permeability experiments using [$^{14}$C]-inulin as a marker. As shown in FIG. 25, [$^{14}$C]-inulin permeability was performed in two additional independent experiments (7.51±0.01×10$^{-6}$ and 7.94±0.03×10$^{-6}$ cm/s; one-way ANOVA, p=0.067; Kruskal-Wallis, p=0.021, Dunn's test, p=0.036) with cells cultured at different passage numbers.

Indirect Contact Coculture

It is well established that changes in culture conditions and cell source can cause significant changes in protein expression of drug metabolizing enzymes, efflux proteins, etc., which are the focus of ongoing studies (Lindley, D. J., et al., *J. Pharm Sci.*, 2012, 101 (4): 1616-1630). In addition, modifications in media have been shown to have considerable effects on BMEC differentiation and tight junction formation. To establish an internal lab control, an indirect coculture model was also run to investigate differences in paracellular permeability when culturing human astrocytes in direct contact with hCMEC/D3 cells. FIG. 26 shows that direct contact leads to a reduction in permeation compared to indirect contact of both [$^{14}$C]-mannitol (1.52±0.07×10$^{-5}$ cm/s and 1.89±0.15×10$^{-5}$ cm/s; t-test, p=0.038; Mann-Whitney, p=0.100), and [$^{14}$C]-sucrose (1.17±0.008×10$^{-5}$ cm/s and 1.53±0.12×10$^{-5}$ cm/s; t-test, p=0.035; Mann-Whitney, p=0.100) respectively.

Passive Transcellular Permeability

To investigate the effects on transcellular permeation when culturing human astrocytes and hCMEC/D3 cells in direct contact, [$^{14}$C]-propranolol apparent permeability was measured. Due to its high lipophilicity, the majority of propranolol is uncharged at physiological pH and is presumed to have minimal paracellular permeation it was selected as a marker for transcellular permeation. FIG. 27 shows that insignificant changes in [$^{14}$C]-Propranolol apparent permeability were seen between hCMEC/D3 and direct contact coculture (1.91±0.19×10$^{-5}$ cm/s and 1.61±0.04×10$^{-5}$ cm/s). This may indicate transcellular permeation through hCMEC/D3 cells followed by passive transport across the human astrocyte layer which don't possess tight junctions. However, these values are nearly 3-fold lower than astrocytes grown in monoculture (4.58±0.41×10$^{-5}$ cm/s). This makes it difficult to delineate the effect of astrocytes on transcellular permeation of [$^{14}$C]-propranolol across the hCMEC/D3 monolayer.

Functional Efflux by Cellular Accumulation

The extent of functional efflux of P-gp in both the monoculture and direct contact coculture was assessed using P-gp substrate rhodamine 123 by measuring cellular accumulation in the presence and absence of an inhibitor, verapamil. As seen in FIG. 28 the presence of verapamil increased total cellular accumulation in both monoculture and coculture models compared to the accumulations without inhibitor (monoculture, 2.8±1.6% to 4.0±0.4%; t-test, p=0.258; Mann-Whitney, p=0.400; coculture, 1.2±1.0% to 2.6±0.4%; t-test, p=0.068; Mann-Whitney, p=0.100). Although this data is not statistically significant (p>0.05) the total accumulation of rhodamine 123 is greater in the hCMEC/D3 monoculture compared to the direct contact coculture.

Due to the importance of limiting paracellular permeation in in vitro BBB cell models, changes in permeation of five paracellular markers of various size; [$^{14}$C]-urea, [$^{14}$C]-mannitol, [$^{14}$C]-sucrose, [$^{14}$C]-PEG-4000, and [$^{14}$C]-inulin were measured (Table 4). When comparing permeation through hCMEC/D3 monolayers to the coculture, all markers trended toward a reduction in paracellular permeation for the direct contact coculture. For the largest marker, PEG-4000, the reduction in permeability in the coculture was the smallest of all markers, however, this isn't unexpected as permeation through the hCMEC/D3 monolayer was sufficiently slow it is unlikely further pore size reduction would lead to sizable changes in permeability.

The reproducibility of the direct contact coculture model is imperative to assess the utility of this model. The permeability of [$^{14}$C]-inulin was used to determine the repeatability of paracellular results across independent experiments. Although there is some difference between the permeability values obtained across multiple experiments, this is to be expected with slight variations in study conditions or cell passage number.

To investigate the impact of direct coculture, an indirect coculture with astrocytes on the basolateral side of the Transwell was also examined. As mentioned, it is often difficult to compare models between different labs due to differences in culture protocol, media selection, passaging, and cell source. Therefore, the indirect model was established under the same conditions and protocols as the direct contact coculture. As was hypothesized, a decrease in [$^{14}$C]-Mannitol and [$^{14}$C]-Sucrose apparent permeabilities were seen when the astrocytes were in direct cell contact, and determined to be significant by the t-test (p<0.05). Further investigation is needed to determine the underlying factors leading to this increased tightness.

To assess passive transcellular permeation the apparent permeability of [$^{14}$C]-propranolol was measured. Propranolol is often used as a passive transcellular marker due to its high octanol:water coefficient leading to almost exclusively transcellular permeation Pade, V. et al., *Pharm. Res.* 1997, 14 (9): 1210-1215). Due to the extra cell layer in the coculture model, it was expected that transcellular permeation would be reduced. While permeability was reduced in the coculture, changes between mono- and coculture weren't significant (p>0.05). To further examine this discrepancy, [$^{14}$C]-propranolol permeability was also measured across human astrocyte monolayers and was found to be approximately three-fold higher than hCMEC/D3 monolayers or the direct contact coculture. This finding validates the coculture permeability data as the hCMEC/D3 cell layer appears to be the rate-limiting barrier to permeation. While astrocytes do play a role in our model, it is unknown if there is a significant contribution of paracellular flux for propranolol that may obfuscate transcellular permeation. While propranolol is unlikely to cross the tight junctions between endothelial cells, astrocyte end feet are known to be much further apart with pores 20-30 Å wide in vivo which may allow greater paracellular movement. Therefore, additional studies are required to understand differences between the apparent permeabilities for hCMEC/D3 and human astrocyte monocultures particularly to elucidate the mechanism of transport across the human astrocyte layer.

Efflux transporters are an important aspect of the BBB as it is a major line of defense to xenobiotics. Rhodamine 123 is a known P-gp substrate and is often used to determine functional expression of P-gp in BMEC cell lines (Lippmann, E. S., et al., *Nature Biotechnology*, 2012, 30 (8), 783-791). Verapamil was used as a P-gp inhibitor to show the difference in total cellular accumulation of rhodamine 123 in its presence. The results of this study showed that rhodamine 123 accumulation is increased in both the monoculture and direct contact coculture models in the presence of verapamil, although there was no significant difference when compared to the absence of inhibitor. The lack of significance may be due to variations in P-gp expression as the hCMEC/D3 cell line increases in passage (Tai, Reddy et al. *Brain Res.* 2009, 1292: 14-24). However, the total accumulation of rhodamine 123 both in the presence and absence of verapamil is greater in the hCMEC/D3 monoculture compared to the coculture, which may suggest that the level of functional efflux is higher when the hCMEC/D3 cells are in direct contact with astrocytes.

Overall, this proof-of-concept study suggests direct contact coculture of human astrocytes and hCMEC/D3 s leads to some tightening of the leaky tight junctions often found in hCMEC/D3 monoculture with minimal modification to other routes of permeation. While this model is still significantly leakier than in vivo conditions it represents an improvement in the paracellular leakage observed in many cell culture models and an advancement in physiologically relevant screening models for determining passive diffusion properties of drugs in the BBB. It should also be noted that while in vivo tightness would be ideal, it may be unnecessary for drug screening. While current TEER values are much lower than found in vivo, it is possible that small changes in tight junction pore radii will lead to very large increases in TEER. Due to the nature of paracellular permeation, these large changes in TEER may have little effect on paracellular permeation due to the difference in the hydrodynamic size of ions being measured (sodium, potassium, calcium, chloride, magnesium, etc vs. drug molecules) (Knipp, G. T. et al, *Pharm Res* 1997, 14 (10): 1332-1340; *J. Pharm Sci.* 1997, 86 (10): 1105-1110). That is, NCEs targeted to the brain are often much larger and more lipophillic molecules than the ions whose movement across the cellular barrier determine TEER. In addition, the vast majority of all NCEs aren't as small or polar as urea, mannitol, or even sucrose. Moreover, TEER values can also be dramatically influenced by several other factors like ionic strength, buffer variations, and temperature that can be confounding variables.

Lastly, species differences are a major cofounder in translation of preclinical screening to humans. Differences in morphology, function, and regulation are all common. Since the common goal is to expedite human translation, it may be better in theory to use a slightly less restrictive human model than a tighter animal model for the screening and ranking of pharmaceutical molecules, provided the human model can discriminate between compounds in series. This will reduce some issues such transport and enzyme affinities and capacities observed between species and better enable an assessment of transcellular permeation in vivo in humans.

As the occurrence of neurological diseases rise along with the number of druggable targets and compounds, a more relevant and robust in vitro cell culture method has become of paramount importance for preclinical screening and lead candidate selection and optimization. The hCMEC/D3 cells have been shown to be functionally similar to primary brain endothelial cells, however, their main downfall has been the presence of leaky tight junctions. These leaky tight junctions obfuscate the delineation of transcellular routes of permeation of many compounds and potentially lead to inaccurate in vivo predictions. Therefore, it is believed that reducing paracellular permeation to levels closer to that found in vivo may lead to a more robust BBB model.

Some promise has been shown in the reduction of paracellular permeability through coculture with astrocytes. However, current models often utilize indirect contact methods in which endothelial cells and astrocytes are separated by the Transwell® permeable support. Here it is shown that direct contact coculture of human astrocytes and hCMEC/D3 cells leads a significant decrease in permeation of paracellular markers, as determined by the t-test. This methodology may serve as a better model for further optimization and in vivo prediction. In addition, seeding of both cell types onto the apical chamber of the Transwell® is likely to be much more conducive to high-throughput screening. Though, further investigation including microscopy, transcriptomic and proteomic analysis, and drug screening must be completed to confirm in vivo relevancy, it is believed that this model is a step in the right direction for enhancing the ability to screen BBB permeation of neurotherapeutic and neurotoxic agents.

Materials

Trypsin, Phosphate Buffered Saline (PBS), Penicillin/Streptomycin, Type I Rat Tail Collagen, Poly-L-Lysine, HEPES (4-(2-hydroxyethyl)-1-piperazineethanesulfonic acid) Buffer, Fibronectin, Maxgel™, Hank's Balanced Salt Solution (HBSS), Hydrocortisone, human Basic Fibroblast Growth Factor (bFGF), Ascorbic Acid, Fetal Bovine Serum (FBS), MaxGel, Fibronectin, Lithium Chloride, Rhodamine-123, and Verapamil were acquired from Sigma-Aldrich Company (St. Louis, Mo.). EBM-2 growth media was manufactured by Lonza Group (Walkersville, Md.). Lipid Concentrate was obtained from BD Biosciences (Sparks, Md.). 0.4 μm Transwell® 12 well plates and T75 flasks were made by Corning Lifesciences (Corning, N.Y.). Radiolabeled compounds were purchased from Moravek Biochemicals Inc. (Brea, Calif.). MTT was obtained from RPI (Mount Prospect, Ill.). The hCMEC/D3 cell line was graciously provided by Dr. Pierre Couraud of the Université Rene Descartes (Paris, France), while human astrocytes, Human Astrocyte Media, and Astrocyte Growth Factor were acquired from ScienCell Research Laboratories (Carlsbad, Calif.).

Cell Culture

The hCMEC/D3 cells were cultured in EBM-2 supplemented with FBS, Penicillin/Streptomycin, bFGF, Hydrocortisone, Ascorbic Acid, Lipid Concentrate, and HEPES buffer. Cells were maintained in a 5% environment at 37° C. HCMEC/D3 cells were passaged when confluence reached approximately 80%, at which time trypsinized cells were placed in a pre-collagenated (Type I) flask. Media was changed every other day. Human astrocytes were cultured under similar conditions in Human Astrocyte Media supplemented with FBS, Astrocyte Growth Factor, and Penicillin/Streptomycin. Cells were passaged approximately every 5 days into flasks pre-coated with Poly-L-Lysine.

Monoculture Studies

In hCMEC/D3 monocultures, cells were seeded at a density of $1\times10^5$ cells/cm$^2$ on Corning Costar 12-well 0.4 μm polyester Transwells® pretreated with 65 μL of 1 mg/mL Type I rat tail collagen and allowed to grow for 7 days. For human astrocyte monocultures, $4\times10^4$ cells were seeded onto Transwells® coated with 2 μg/cm$^2$ poly-L-lysine and grown for 9 days prior to permeability studies.

Indirect Coculture Studies

Indirect coculture Transwells® were first pretreated with 65 μL of 1 mg/mL Type I rat tail collagen in ethanol in the apical chamber and left to evaporate for 4 hours. Following evaporation, the Transwells® were flipped and 2 m/cm$^2$ poly-L-lysine was added to the basolateral side of the Transwells® and left overnight. Human astrocytes were plated on the basolateral side of the flipped Transwells® at a density of $4\times10^4$ cells/cm$^2$ and left to attach for 4 hours. Transwells® were then placed into the normal orientation and grown for 48 hours. After this time, hCMEC/D3 cells were plated in the apical compartment at a density of $1\times10^5$ cells/cm$^2$. The coculture was left to proliferate/differentiate in EBM-2 for an additional 7 days with media changes every other day before the permeability studies were conducted.

Direct Coculture Studies

For direct coculture studies, Transwell® inserts were coated with 2 μm/cm$^2$ poly-L-lysine and left overnight. Human astrocytes were then plated at a density of $4\times10^4$ cells/cm$^2$. Astrocytes were allowed to proliferate/differentiate for 48 hours in astrocyte media. After 48 hours, media was removed and hCMEC/D3 s were plated in EBM-2 at a density of $1\times10^5$ cells/cm$^2$. The coculture was grown in EBM-2 with media changes every other day for an additional 7 days before studies were conducted.

Direct Coculture Optimization

Optimization of the direct coculture was studied separately by utilizing a number of media additives at varying concentrations. Hydrocortisone was studied at 1.4 μM and 100 nM, while lithium chloride was studied separately at 0-10 mM, each at the start of hCMEC/D3 seeding or at Day 2 and maintained throughout culturing. The impact of HEPES concentration in media was observed utilizing 10-50 mM concentrations upon the start of hCMEC/D3 plating. All culture conditions were the same as stated above throughout optimization. Degree of optimization was tested utilizing [C14]-Mannitol as a paracellular marker, with permeability studies performed.

Direct Triculture Systems

In order to establish a triculture model of the BBB, a determination of cell seeding density ratios of BMECs to pericytes and astrocytes that would provide significantly increased resistance comparative to the monoculture as observed by TEER was sought. TEER trends corresponding to various seeding density ratios were evaluated, and the seeding density ratio was selected based on stability in the TEER trend upon achieving a statistically significant steady state increase in electrical resistance.

Briefly, and by way of example, Corning Transwells® (polyester clear 3460, 12 well format) were first incubated with PLL for 30 minutes. Excess PLL solution was then removed by aspiration, and differing seeding densities of primary astrocytes (ScienCell Research) were plated and cultured on the apical side of the filter support until they reached confluency by visualization under an inverted microscope (two days later) in recommended astrocyte media. Prior to seeding primary pericytes (ScienCell Research) onto the astrocytes monoculture, the astrocyte conditioned media was aspirated and the cells were washed 2× with sterile Phosphate Buffered Saline (PBS; pH 7.4) solution. Next, PLL was added on top of the astrocytes for approximately 15 minutes. Excess PLL was then removed and differing densities of pericytes were plated onto the astrocytes monolayer. The coculture was maintained with recommended pericyte media on the apical side and astrocyte media on the basolateral side for two days. Before plating BMECs onto the direct coculture, the media is aspirated and the coculture was washed 2× with PBS and incubated with rat tail collagen type I for 15 minutes. Excess collagen was removed and then the different seeding densities of the BMECs were plated onto the coculture to form a direct triculture configuration. The triculture was then maintained under endothelial cell media (EBM-2) on the apical side and astrocyte media on the basolateral side.

Cell Viability Assay

Cell viability in the presence of various HEPES concentrations was inferred by the mitochondrial oxidation of 3-(4,5-dimethylthiazol-2-yl)-2,5-diphenyltetrazolium bromide (MTT) dye. The direct contact coculture was plated in a 96-well plate following the same methods as stated above. On Day 7 post hCMEC/D3 plating, media containing HEPES was removed and replaced with 190 µL, fresh media and 10 µL of 5 mg/mL MTT and incubated at 37° C. with 5% $CO_2$ for 4 hours. MTT was then removed and replaced with 200 µL DMSO and left agitating at room temperature for 1 hour. Absorbance at 570 nm was determined using a plate reader. Cell viability was normalized to 10 mM HEPES control. Assays were performed with n=6.

Permeability Studies

Permeability studies were performed at 37° C. on a rocker plate in triplicate using [C14]-labeled markers ([C14]-Urea, [C14]-Mannitol, [C14]-Sucrose, [C14]-Inulin, [C14]-PEG-4000, and [C14]-Propranolol) at a concentration of 0.25 µCi/mL in HBSS. In all studies, human astrocytes ranged from passages 6-12 while hCMEC/D3 cells ranged from passage 36-48. Before all permeability studies, cells were washed twice with PBS before equilibrating in HBSS for 20 minutes shortly before the study. After study initiation, 100 µL samples were taken at 15, 30, 45, 60, and 90 minute time points. 4 mL of scintillation cocktail was added for analysis by scintillation counting. Permeability coefficients (cm/s) were obtained through the following equation:

$$P_{apparent} = \frac{\frac{dM}{dt}}{C_0 * SA * 60}$$

where $$\frac{dM}{dt}$$

is the rate of radionucleotide transfer across the cell layer, $C_0$ is the initial donor concentration, SA is the surface area of the Transwell® filter support, and 60 represents a correction factor from minutes to seconds.

Functional Efflux

Monoculture and coculture cells were plated on a 96-well plate to assess cellular accumulation of rhodamine 123. Studies were performed at 37° C. on a rocking platform. Cells were incubated with 5 µM rhodamine 123 in HBSS for 1 hr. Inhibition studies were performed by first pre-incubating cells with 10 µM verapamil in HBSS for 30 minutes at 37° C. Cells were then incubated with both substrate and inhibitor for 1 hr. Following 1 hr incubation, cells were washed with PBS and lysed with buffer containing 20 mM Tris, 100 mM NaCl, 1 mM EDTA, and 1% Triton X-100. Samples were analyzed by measuring fluorescence with an excitation of 485 nm and emission of 535 nm using a plate reader. All experiments were conducted in triplicate (n=3).

Statistics

The distribution of permeability coefficients across the brain has not been well studied; however, some studies involving other membranes suggest that permeability can be normally or log-normally distributed based on the compound (Frum, Y., et al., *Eur. J. Pharm Biopharm.* 2007, 67 (2): 434-439; Khan, G. M., et al., *Int. J. Phar.* 2005, 303 (1-2): 81-87). Therefore, the data presented here has been subjected to both parametric and non-parametric tests. Studies were compared using the Mann-Whitney test or the Kruskal-Wallis test with a Dunn's post-hoc test. Additionally, all studies were also subjected to a two-tailed unpaired student's t-test or one-way ANOVA with a Bonferroni post-hoc test. Studies with p-values less than 0.05 were considered to have significant differences.

While various embodiments of blood brain barrier models and methods to generate and use the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

While illustrated examples, representative embodiments and specific forms of the invention have been illustrated and described in detail in the drawings and foregoing description, the same is to be considered as illustrative and not restrictive or limiting. The description of particular features in one embodiment does not imply that those particular features are necessarily limited to that one embodiment. Features of one embodiment may be used in combination with features of other embodiments as would be understood by one of ordinary skill in the art, whether or not explicitly described as such. Exemplary embodiments have been shown and described, and all changes and modifications that come within the spirit of the invention are desired to be protected.

What is claimed is:

1. A method for preparing a direct-contact cell culture blood brain barrier model system comprising the steps of:
    a) preparing a cell culture plate with a permeable membrane support;
    b) seeding a first, astrocyte or other glial cell line on said membrane support and proliferating said first cell line for about two days in the presence of a cell culture medium;
    c) removing said cell culture medium and washing proliferated cells of said first, astrocyte or other glial cell line;

d) seeding a second, endothelial or preprogrammed induced pluripotent stem cell line over proliferated cells of said first, astrocyte or other glial cell line whereby both the first, astrocyte or other glial cell line and the second, endothelial or preprogrammed induced pluripotent stem cell line are on the same side of the permeable membrane;

e) proliferating said second, endothelial or preprogrammed induced pluripotent stem cell line and first, astrocyte or other glial cell line in the presence of cell culture medium; and f) replacing cell culture medium every other day until proliferated cells reach confluency as determined by stabilized normalized Transendothelial Electrical Resistance (TEER) or by other established methods of assessing cell proliferation or differentiation.

2. The method of claim 1 further comprising a step of: seeding a third, pericyte cell line over the proliferated cells of said first, astrocyte or other glial cell line and proliferating said third, pericyte cell line for about two days in the presence of a culture medium before step d).

3. The method of claim 2, wherein said second cell line is brain microvessel endothelial cells (BMECs) of human or animal origin, primary, immortalized, normal or in a diseased state, or Human Brain Endothelial Cells (HBECs).

4. A method to determine or predict drug delivery efficacy and/or toxicity of a drug candidate using a cell culture system prepared according to claim 2.

5. A cell culture system prepared according to the method of claim 2.

6. The cell culture system of claim 5, wherein said second cell line is BMECs of human or animal origin, primary, immortalized, normal or in a diseased state, or HBECs.

7. The cell culture system of claim 6, wherein said second cell line is proliferative human derived cerebral microvessel endothelial cells hCMEC/D3.

8. The cell culture system of claim 5, wherein said second cell line is preprogrammed induced pluripotent stem cells.

9. The method of claim 1, wherein said second cell line is BMECs of human or animal origin, primary, immortalized, normal or in a diseased state, or HBECs.

10. The method of claim 1, wherein said second cell line is BMECs of human or animal origin, primary, immortalized, normal or in a diseased state, or HBECs.

11. The method of claim 10, wherein said second cell line is proliferative human derived cerebral microvessel endothelial cells hCMEC/D3.

12. The method of claim 10, wherein said second cell line is preprogrammed induced pluripotent stem cells.

13. A method to determine or predict drug delivery efficacy and/or toxicity of a drug candidate using a cell culture system prepared according to claim 1.

14. The method of claim 1, wherein said permeable membrane support or cell culture surface is pre-conditioned with poly-L-lysine or other selected extracellular matrix overnight before plating said first, astrocyte or other glial cell line.

15. The method of claim 1, wherein said cell culture medium is a buffered medium comprising fetal bovine serum, penicillin streptomycin, and growth factors.

16. A cell culture system prepared according to the method of claim 1.

17. The cell culture system of claim 16, wherein said second, endothelial or preprogrammed induced pluripotent stem cell line is BMECs of human or animal origin, primary, immortalized, normal or in a diseased state, or HBECs.

18. The cell culture system of claim 17, wherein said second cell line is proliferative human derived cerebral microvessel endothelial cells hCMEC/D3.

19. The cell culture system of claim 16, wherein said second cell line is preprogrammed induced pluripotent stem cells.

20. A direct-contact cell culture blood brain barrier model system prepared according to the steps of:
   a. preparing a cell culture plate with a permeable membrane support;
   b. seeding astrocytes or other glial cells on said membrane support and proliferating said astrocytes or other glial cells for about two days in the presence of a cell culture medium;
   c. removing said cell culture medium and washing proliferated astrocytes or other glial cells;
   d. seeding pericytes over said astrocytes or other glial cells and proliferating said pericytes for about two days in the presence of a cell culture medium, whereby both the astrocytes or other glial cells and the pericytes are on the same side of the permeable membrane support;
   e. removing said cell culture medium and washing proliferated pericytes;
   f. seeding brain micro vessel endothelial cells (BMECs) of human or animal origin, primary, immortalized, normal or in a diseased state, over said pericytes and astrocytes or other glial cells;
   g. proliferating said BMECs, pericytes, and astrocytes or other glial cells in the presence of cell culture medium; and
   h. replacing cell culture medium every other day until the cells reach confluency as determined by stabilized normalized Transendothelial Electrical Resistance (TEER) significantly greater than that of a BMEC monoculture or by other established methods of assessing proliferation or differentiation.

21. The cell culture system of claim 20, wherein said BMECs are human cerebral micro vessel endothelial cells hCMEC/D3.

* * * * *